US008147843B2

(12) United States Patent
Hill et al.

(10) Patent No.: US 8,147,843 B2
(45) Date of Patent: *Apr. 3, 2012

(54) CD95L OR TRAIL FUSION PROTEINS

(75) Inventors: Oliver Hill, Neckarsteinach (DE);
Christian Gieffers, Dossenheim (DE);
Meinolf Thiemann, Shriesheim (DE)

(73) Assignee: Apogenix GmbH, Heidelberg (DE)

( * ) Notice: Subject to any disclaimer, the term of this patent is extended or adjusted under 35 U.S.C. 154(b) by 270 days.

This patent is subject to a terminal disclaimer.

(21) Appl. No.: 12/439,486

(22) PCT Filed: Aug. 28, 2007

(86) PCT No.: PCT/EP2007/007517
§ 371 (c)(1),
(2), (4) Date: Feb. 27, 2009

(87) PCT Pub. No.: WO2008/025516
PCT Pub. Date: Mar. 6, 2008

(65) Prior Publication Data
US 2011/0027218 A1 Feb. 3, 2011

(30) Foreign Application Priority Data

Aug. 28, 2006 (EP) .................... 06017891

(51) Int. Cl.
*A61K 39/00* (2006.01)
*A61K 38/00* (2006.01)
*C07K 14/525* (2006.01)
*C12N 15/00* (2006.01)
(52) U.S. Cl. .............. 424/192.1; 530/351; 536/23.4; 514/1.4; 435/455
(58) Field of Classification Search ............ None
See application file for complete search history.

(56) References Cited

FOREIGN PATENT DOCUMENTS
EP   1365027 A2   11/2003

OTHER PUBLICATIONS

Belousova, Natalya et al.; "Genetically Targeted Adenovirus Vector Directed to CD40-Expressing Cells"; 2003, *Journal of Virology*, vol. 77, No. 21, pp. 11367-11377.
Efimov, Vladimir P. et al.; "Bacteriophage T4 as a Surface Display Vector"; 1995, *Virus Genes*, vol. 10, No. 2, pp. 173-177.
Frank, Sabine et al.; "Stabilization of Short Collagen-like Triple Helices by Protein Engineering"; 2001, *J. Mol. Biol.*, vol. 308, pp. 1081-1089.
Krasnykh, Victor et al.; "Genetic Targeting of an Adenovirus Vector via Replacement of the Fiber Protein with the Phage T4 Fibritin"; 2001, *Journal of Virology*, vol. 75, No. 9, pp. 4176-4183.
Meier, Sebastian et al.; "Foldon, The Natural Trimerization Domain of T4 Fibritin, Dissociates into a Monomeric A-state Form containing a Stable β-Hairpin: Atomic Details of Trimer Dissociation and Local β-Hairpin Stability from Residual Dipolar Couplings"; 2004, *J. Mol. Biol.*, vol. 344, pp. 1051-1069.
Miroshnikov, Konstantin A. et al.; Engineering trimeric fibrous proteins based on bacteriophage T4 adhesins; 1998, *Protein Engineering*, vol. 11, No. 4, pp. 329-332.
Sissoëff, Ludmilla et al.; "Stable trimerization of recombinant rabies virus glycoprotein ectodomain is required for interaction with the $p75^{NTR}$ receptor"; 2005, *Journal of General Virology*, vol. 86, pp. 2543-2552.
Shiraishi, Tetsuya et al.; "Increased cytotoxicity of soluble Fas Ligand by fusing isoleucine zipper motif"; 2004, *Biochemical and Biophysical Research Communications*, vol. 322, pp. 197-202.
Sun, Kuang-Hui et al.; "Expression, purification, refolding, and characterization of recombinant human soluble-Fas ligand from *Escherichia coli*"; 2005, *Enzyme and Microbial Technology*, vol. 36, No. 4, pp. 527-534.
Yang, Xinzhen et al.; "Highly Stable Trimers Formed by Human Immunodeficiency Virus Type 1 Envelope Glycoproteins Fused with the Trimeric Motif of T4 Bacteriophage Fibritin"; 2002, *Journal of Virology*, vol. 76, No. 9, pp. 4634-4642.
"Wac fibritin neck whiskers"; 2003, retrived from EBI accession No. UNIPROT: Q7Y4X5, 1 page.

*Primary Examiner* — Elly-Gerald Stoica
(74) *Attorney, Agent, or Firm* — Perkins Coie LLP; Viola T. Kung

(57) ABSTRACT

The present invention refers to fusion proteins comprising a TNF superfamily (TNFSF) cytokine or a receptor binding domain thereof fused to a trimerization domain and a nucleic acid molecule encoding the fusion protein. The fusion protein is present as a trimeric complex or as an oligomer thereof and is suitable for therapeutic, diagnostic and/or research applications.

24 Claims, 6 Drawing Sheets

| Protein | SEC Elution in ml | Mw in kDa | Log Mw |
|---|---|---|---|
| Thyroglobulin | 9.82 | 670 | 5.826 |
| γ-Globulin | 12.97 | 158 | 5.199 |
| Ovalbumin | 15.44 | 44 | 4.643 |
| Myoglobin | 17.43 | 17 | 4.230 |
| Vitamin B12 | 20.65 | 1.4 | 3.130 |
| | | | |
| CD95 Ligand (hs95L-AT4) | 13.85 | _90.3_ | 4.956 |

Purification of hsCD95-A69

Purification of hsTRAIL-AT4:

CD95L OR TRAIL FUSION PROTEINS

CROSS-REFERENCE TO RELATED APPLICATIONS

This application is a U.S. National Stage Application of PCT/EP2007/007517, filed Aug. 28, 2007, which claims the benefit of European Application No. 06017891.0, filed Aug. 28, 2006, the contents of which are hereby incorporated by reference in their entirety.

The present invention refers to fusion proteins comprising a TNF superfamily (TNFSF) cytokine or a receptor binding domain thereof fused to a trimerization domain and a nucleic acid molecule encoding the fusion protein. The fusion protein is present as a trimeric complex or as an oligomer thereof and is suitable for therapeutic, diagnostic and/or research applications.

STATE OF THE ART

It is known that trimerization of TNSF cytokines, e.g., the CD95 ligand (CD95L), is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the CD95L-receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of hepta-d-repeats in the coiled-coil zipper motif are difficult to determine. In addition, coiled-coil structures have the tendency to form macromolecular aggregates after alteration of pH and/or ionic strength.

It was an object of the present invention to provide fusion proteins comprising a TNF cytokine or a receptor binding domain thereof, which allow efficient recombinant manufacture combined with good trimerization properties.

SUMMARY OF THE INVENTION

The present invention relates to a fusion protein comprising
(i) a TNF-superfamily cytokine or a receptor binding domain thereof
(ii) a flexible linker element between components (i) and (iii), and
(iii) a fibritin trimerization domain.

The invention further relates to a nucleic acid molecule encoding a fusion protein as described herein and to a cell or a non-human organism transformed or transfected with a nucleic acid molecule as described herein.

The invention also relates to a pharmaceutical or diagnostic composition comprising as an active agent a fusion protein, a nucleic acid molecule, or a cell as described herein.

The invention also relates to a fusion protein, a nucleic acid molecule, or a cell as described herein for use in therapy, e.g., the use of a fusion protein, a nucleic acid molecule, or a cell as described herein for the preparation of a pharmaceutical composition in the prophylaxis and/or treatment of disorders caused by, associated with and/or accompanied by dysfunction of TNF cytokines, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

B) Analysis of hs95L-AT4 SEC fractions by SDS-PAGE silver stain: SEC fractions shown in A were separated by SDS-PAGE and subsequently analysed by silver staining. The fraction number and the molecular weight (in kDa) of standard proteins is indicated.

Figure 2:
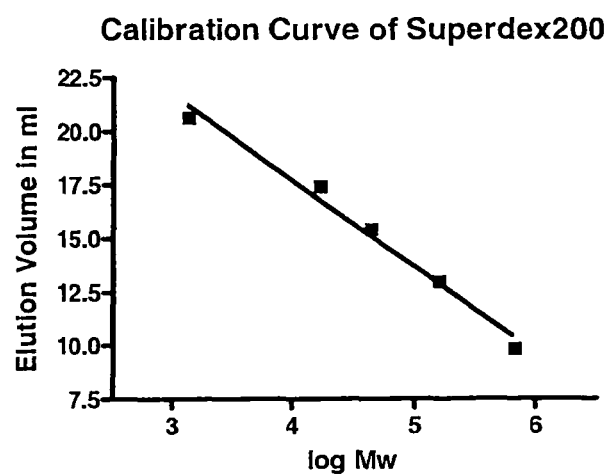

FIG. 2: Determination of the native apparent molecular weight for hs95L-AT4

The apparent molecular weight of purified hs95L-AT4 was determined based on calibration of the Superdex 200 column with gel filtration standard proteins (Bio-Rad GmbH, München, Germany). The elution volume of the calibration standards were plotted against the logarithm of the respective molecular weights to create a calibration curve. The apparent Mw of hs95L-AT4 was calculated based on the respective elution volume of 13.85 ml. The table summarizes the results of the SEC analysis.

Figure 3:
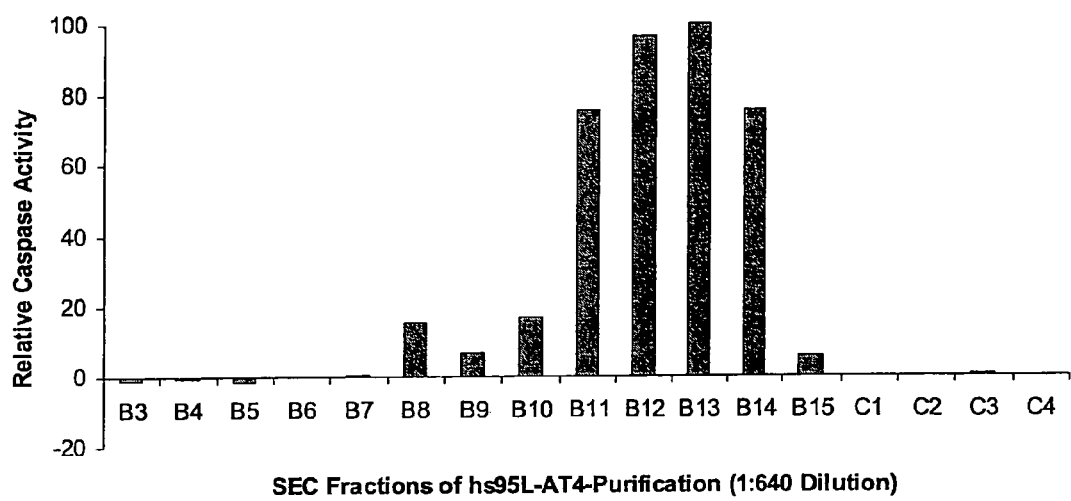

FIG. 3: Analysis of hs95L-AT4 SEC fractions (shown in FIG. 1) by their potential to induce apoptosis in Jurkat cells. The protein content of the SEC fractions matches their ability to induce Caspase activity.

Figure 4:
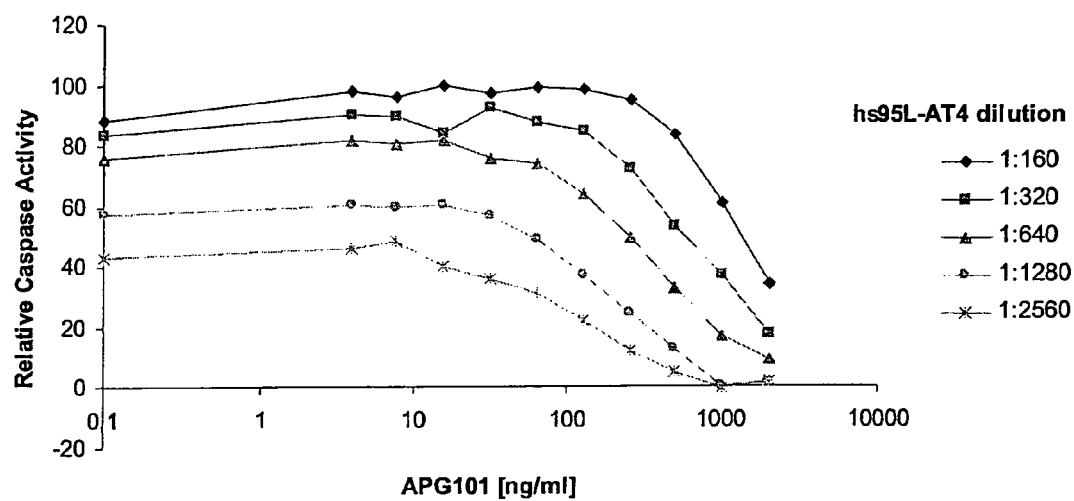

FIG. 4: Inhibition of hs95L-AT4 induced apoptosis by APG101 Hs95L-AT4 was incubated for 30 min with different amounts of APG101, added to Jurkat cells and subsequently apoptosis was measured by analysing caspase activity. The graphic shows the dose dependent antagonizing effect of APG101 on hsCD95-AT4 induced apoptosis.

Figure 5:
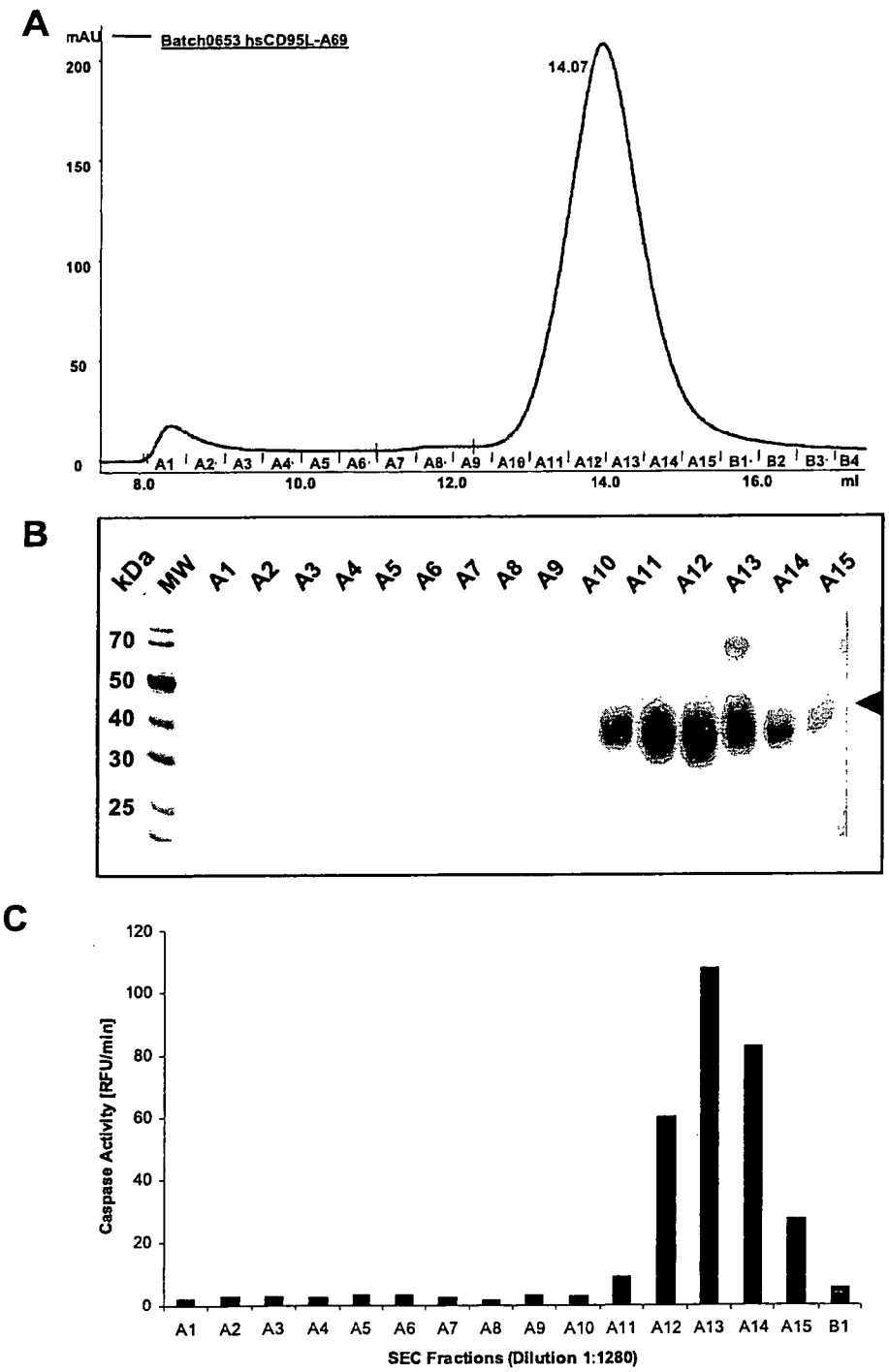

FIG. 5: A) SEC analysis of Streptactin affinity purified hs95L-A69: Affinity purified protein eluted by desthiobiotin from immobilized Streptactin was loaded onto a Superdex200 column. The protein elution profile of the SEC run was measured at OD280. The retention volume of the respective hs95L-A69 peak and the fraction numbers are indicated.

B) Analysis of SEC fractions by SDS-PAGE silver stain: SEC fractions shown in A were separated by SDS-PAGE and subsequently analysed by silver staining. The fraction number and the molecular weight (in kDa) of standard proteins is indicated.

C) Analysis of hs95L-A69SEC fractions (shown in A) by their potential to induce apoptosis in Jurkat cells. The protein content of the SEC fractions matches their ability to induce Caspase activity.

Figure 6:
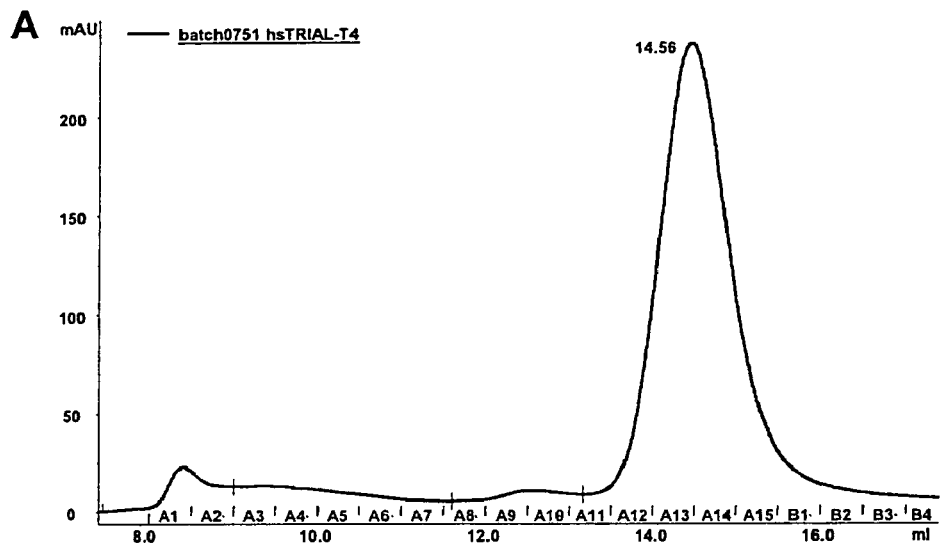
Figure 6:
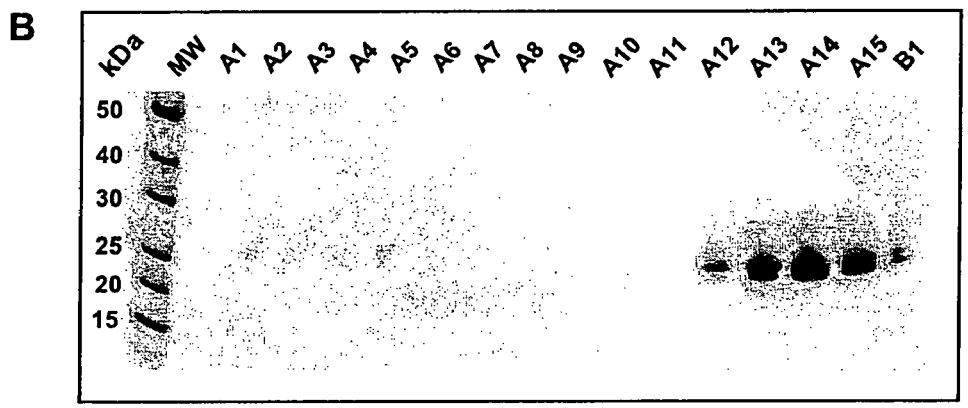
Figure 6:
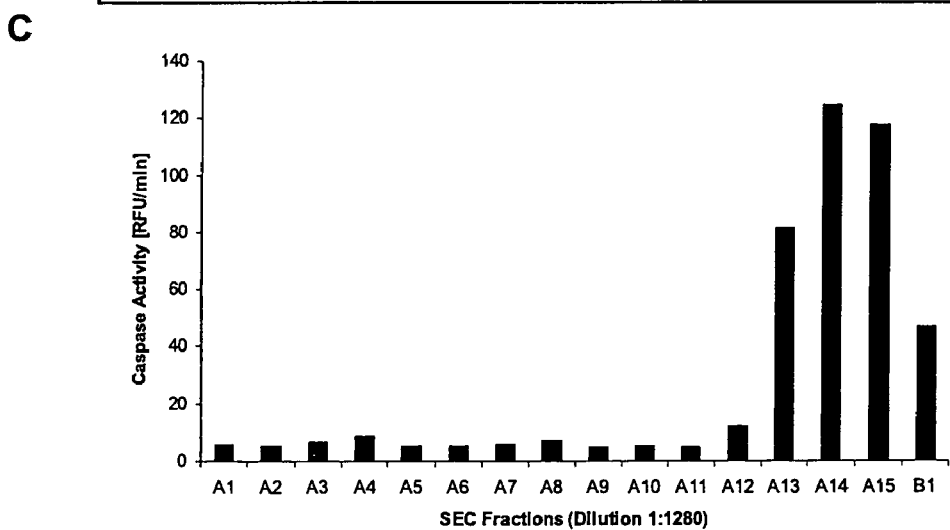

FIG. 6: A) SEC analysis of Streptactin affinity purified hsTRAIL-AT4: Affinity purified protein eluted by desthiobiotin from immobilized Streptactin was loaded onto a Superdex200 column. The protein elution profile of hsTRAIL-AT4 peak and the fraction numbers are indicated.

B) Analysis of hsTRAIL-AT4 SEC fractions by SDS-PAGE silver stain: SEC fractions shown in A were separated by SDS-PAGE and subsequently analysed by silver staining. The fraction number and the molecular weight (in kDa) of standard proteins is indicated.

C) Analysis of hsTRAIL-AT4 SEC fractions (shown in A) by their potential to induce apoptosis in Jurkat cells. The protein content of the SEC fractions matches their ability to induce Caspase activity.

DETAILED DESCRIPTION OF THE INVENTION

Thus, the present invention relates to a fusion protein comprising
(i) a TNF-superfamily cytokine or a receptor binding domain thereof
(ii) a flexible linker element between components (i) and (iii), and
(iii) a fibritin trimerization domain.

The fusion protein may be a monomeric protein or a multimeric protein. Preferably, the fusion protein is present as a trimeric complex consisting of three monomeric units which may be identical or different. Preferably, a trimeric complex consists of three identical fusion proteins. The trimeric complex as such shows biological activity. It was found, however, that oligomers of the trimeric complex, e.g. defined complexes wherein the basic trimeric structure is present 2, 3 or 4 times, also have biological activity.

Component (i) of the fusion protein is a cytokine of the TNF superfamily or a receptor binding domain thereof. Preferably, component (i) is a mammalian, particularly human cytokine or a receptor binding domain thereof including allelic variants and/or derivatives thereof. Further, it is preferred that the TNF cytokine is a receptor binding domain thereof capable of binding to the corresponding cytokine receptor and preferably capable of receptor activation, whereby apoptotic or proliferative activity may be caused. The cytokine may e.g. be selected from TNF superfamily members, e.g. human TNFSF-1 to -18 as indicated in Table 1, preferably from LTA (SEQ ID NO:25), TNFα (SEQ ID NO:26), LTB (SEQ ID NO:27), OX40L (SEQ ID NO:28), CD40L (SEQ ID NO:29), CD95L (SEQ ID NO:30), CD27L (SEQ ID NO:31), CD30L (SEQ ID NO:32), CD137L (SEQ ID NO:33), TRAIL (SEQ ID NO:34), RANKL (SEQ ID NO:35), TWEAK (SEQ ID NO:36), APRIL 1 (SEQ ID NO:37), APRIL 2 (SEQ ID NO:38), BAFF (SEQ ID NO:39), LIGHT (SEQ ID NO:40), TL1A (SEQ ID NO:41), GITRL (SEQ ID NO:42), EDA-A1 (SEQ ID NO:43), EDA-A2 (SEQ ID NO:44), or a receptor binding domain thereof. Preferred receptor binding domains of the respective proteins are indicated in Table 1 (NH$_2$-aa to COOH-aa) and, e.g., comprise amino acids 59-205 or 60-205 of LTA (SEQ ID NO:25), 86-233 of TNFα (SEQ ID NO:26), 82-244 or 86-244 of LTB (SEQ ID NO:27), 52-183 or 55-183 of OX40L (SEQ ID NO:28), 112-261 or 117-261 of CD40L (SEQ ID NO:29), 51-193 or 56-193 of CD27L (SEQ ID NO:31), 97-234, 98-234 or 102-234 of CD30L (SEQ ID NO:32), 86-254 of CD137L (SEQ ID NO:33), 161-317 of RANKL (SEQ ID NO:35), 103-249, 104-249 or 105-249 of TWEAK (SEQ ID NO:36), 112-247 of APRIL 1 (SEQ ID NO:37), 112-250 of APRIL 2 (SEQ ID NO:38), 140-285 of BAFF (SEQ ID NO:39), 91-240 of LIGHT (SEQ ID NO:40), 91-251 or 93-251 of TL1A (SEQ ID NO:41), 52-177 of GITRL (SEQ ID NO:42), 245-391 of EDA-A1 (SEQ ID NO:43), 245-389 of EDA-A2 (SEQ ID NO:44).

More preferably, component (i) is selected from CD95L, TRAIL or TNFα or a receptor binding domain thereof. In an especially preferred embodiment, component (i) comprises the extracellular portion of a TNF cytokine including the receptor binding domain without membrane located domains. In an especially preferred embodiment, component (i) of the recombinant fusion protein is selected from human CD95L, particularly amino acids 142-281 or 144-281 of SEQ ID NO:30, or human TRAIL, particularly amino acids 116-281, 118-281 or 120-281 of SEQ ID NO:34.

In a further preferred embodiment of the invention, the cytokine of the TNF superfamily or a receptor binding domain thereof, e.g., TRAIL, of the fusion protein as described herein comprises a mutant of the cytokine of the TNF superfamily or a receptor binding domain thereof which binds and/or activates TRAIL-receptor 1 (TRAILR1) and/or TRAIL-receptor 2 (TRAILR2). The binding and/or activity of the mutant may be, e.g., determined by the assays as disclosed in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270).

The mutant may be generated by any technique and is known by the skilled person, e.g., the techniques disclosed in an der Sloot et al. (PNAS, 2006, 103:8634-8639), Kelley et al. (J. Biol. Chem., 2005, 280:2205-2215), or MacFarlane et al. (Cancer Res., 2005, 65: 11265-11270) any may comprise any type of structural mutations, e.g., substitution, deletion, duplication and/or insertion of an amino acid. A preferred embodiment is the generation of substitutions. The substitution may affect at least one amino acid of the cytokine of the TNF superfamily or a receptor binding domain thereof as described herein. In a preferred embodiment, the substitution may affect at least one of the amino acids of TRAIL, e.g., human TRAIL (e.g., SEQ ID NO:34). Preferred substitutions in this regard affect at least one of the following amino acids of human TRAIL of SEQ ID NO:34: R130, G160, Y189, R191, Q193, E195, N199, K201, Y213, T214, S215, H264, I266, D267, D269. Preferred amino acid substitutions of human TRAIL of SEQ ID NO:34 are at least one of the following substitutions: R130E, G160M, Y189A, Y189Q, R191K, Q193S, Q193R, E195R, N199V, N199R, K201R, Y213W, T214R, S215D, H264R, I266L, D267Q, D269H, D269R, or D269K.

The amino acid substitution(s) may affect the binding and/or activity of TRAIL, e.g., human TRAIL, to or on either the TRAILR1 or the TRAILR2. Alternatively, the amino acid substitution(s) may affect the binding and/or activity of TRAIL, e.g., human TRAIL, to or on both, the TRAILR1 and the TRAILR2. The binding and/or activity of the TRAILR1 and/or TRAILR2 may be affected positively, i.e., stronger, more selective or specific binding and/or more activation of the receptor. Alternatively, the binding and/or activity of the TRAILR1 and/or TRAILR2 may be affected negatively, i.e., weaker, less selective or specific binding and/or less or no activation of the receptor.

Examples of mutants of TRAIL with amino acid substitution(s) of the invention that affect binding and/or activity of both TRAILR1 and TRAILR2 may be found, e.g., in Table 1 of MacFarlane et al. (cf. above) and may comprise a human TRAIL mutant with the following two amino acid substitutions of SEQ ID NO:34 Y213W and S215D or with the following single amino acid substitution Y189A.

Examples of mutants of TRAIL with amino acid substitution(s) of the invention that affect binding and/or activity of TRAILR1 may be found, e.g., in Table 1 of MacFarlane et al. (cf. above) and may comprise a human TRAIL mutant with the following four amino acid substitutions of SEQ ID NO:34 N199V, K201R, Y213W and S215D or with the following five amino acid substitutions Q193S, N199V, K201R, Y213W and S215D or may be found in Table 2 of Kelley et al. (cf. above) and may comprise a human TRAIL mutant with the following six amino acid substitutions Y213W, S215D, Y189A, Q193S, N199V, and K201R or with Y213W, S215D, Y189A, Q193S, N199R, and K201R.

Examples of mutants of TRAIL with amino acid substitution(s) of the invention that affect binding and/or activity of TRAILR2 may be found, e.g., in Table 1 of MacFarlane et al. (cf. above) or in Table 2 of Kelley et al. (cf. above) and may comprise a human TRAIL mutant with the following six amino acid substitutions of SEQ ID NO:34 Y189Q, R191K, Q193R, H264R, I266L, and D267Q or may be found in Table 2 of van der Sloot et al. (cf. above) and may comprise a human TRAIL mutant with the following single amino acid substitution D269H, with the following two amino acid substitutions D2691H and E195R or with D269H and T214R.

Thus one preferred embodiment is a fusion protein as described herein wherein component (i) comprises a mutant of TRAIL or of a receptor binding domain thereof which binds and/or activates TRAILR1 and/or TRAILR2.

One preferred embodiment of a fusion protein comprising a mutant of TRAIL or of a receptor binding domain as described herein is a fusion protein wherein component (i) comprises at least one amino acid substitution.

Such an amino acid substitution affects at least one of the following amino acid positions of human TRAIL (SEQ ID NO:34): R130, G160, Y189, R191, Q193, E195, N199, K201, Y213, T214, S215, H264, I266, D267, D269.

Such an amino acid substitution is at least one of the following: R130E, G160M, Y189A, Y189Q, R191K, Q193S, Q193R, E195R, N199V, N199R, K201R, Y213W, T214R, S215D, H264R, I266L, D267Q, D269H, D269R, or D269K.

Component (ii) is a flexible linker element located between components (i) and (iii). The flexible linker element preferably has a length of 5-20 amino acids, particularly a length of 6, 9, 12, 15 or 18 amino acids. The linker element is preferably a glycine/serine linker, i.e. a peptide linker substantially consisting of the amino acids glycine and serine. In an especially preferred embodiment, the linker has the amino acid sequence $(GSS)_a(SSG)_b(GS)_c(S)_d$, wherein a, b, c, d is each 0, 1, 2, 3, 4, or 5 (SEQ ID NO:45). Examples of specific linker sequences are GSS GSS GSS GS (a=3 b=0, b=0, c=1; d=0) (SEQ ID NO:46) (see also amino acids 161-171 of SEQ ID NO: 19 or amino acids 182-192 of SEQ ID NO:20), or SSG SSG SSG S (a=0; b=3, c=0; d=1) SEQ ID NO:47). It is clear to the skilled person that in cases in which the cytokine of the TNF superfamily or a receptor binding domain thereof already terminates with a G, e.g. human TRAIL (SEQ ID NO:34) such a G may form the first G of the linker in the linker sequence $(GSS)_a(SSG)_b(GS)_c(S)_d$ (see amino acid 182 of SEQ ID NO:20).

Component (iii) is a fibritin trimerization domain, particularly a bacteriophage fibritin trimerization domain, more particularly a fibritin trimerization domain from bacteriophage T4 or related bacteriophages such as T—even bacteriophages or phage RB69 or phage AR1 as shown in Table 2. The T4 fibritin trimerization domain is e.g. described in U.S. Pat. No. 6,911,205 or WO 01/19958, the contents of which is herein incorporated by reference. T4 fibritin has the sequence of SEQ ID NO:23, and its trimerization domain is set forth in SEQ ID NO:8 and at residues 458-484 of SEQ ID NO:23. RB69 fibritin has the sequence of SEQ ID NO:24 and its trimerization domain is set forth in SEQ ID NO:9 and at residues 455-480 of SEQ ID NO:24.

More preferably, component (iii) comprises the amino acid sequence (G) YIPEAPRDGQ AYVRKDGEWV LLSTFL (SEQ ID NO:8 or amino acids 458-484 or 459-484 of SEQ ID NO:23) or a sequence variant having an identity of at least 70%, 75%, 80%, 85%, 90%, 95%, 96%, 97%, 98% or 99% thereto. Examples of preferred sequence variants are shown in Table 3.

More preferably, component (iii) comprises the amino acid sequence (G) YIEDAPSDGKFYVRKDGAWVELPTA (SEQ ID NO:9 or amino acids 455-480 or 456-480 of SEQ ID NO:24) or a sequence variant having an identity of at least 70%, 75%, 80%, 85%, 90%, 95%, 96%, 97%, 98% or 99% thereto.

Further, it is preferred that component (iii) has a length of from 20 up to 30 amino acids.

In the fusion protein of the invention, it is preferred that component (i) is located N-terminally of component (iii). The invention, however, also refers to embodiments, wherein component (iii) is located N-terminally of component (i). The components (i) and (iii) may directly flank each other or be separated by, e.g., a linker sequence as described herein (see, e.g., SEQ ID NOs:19 and 20).

The fusion protein may additionally comprise an N-terminal signal peptide domain, which allows processing, e.g. extracellular secretion, in a suitable host cell. Preferably, the N-terminal signal peptide domain comprises a protease, e.g. a signal peptidase cleavage site and thus may be removed after or during expression to obtain the mature protein. Further, the fusion protein may additionally comprise a C-terminal flexible element, having a length of e.g. 1-50, preferably 10-30 amino acids which may include or connect to a recognition/purification domain, e.g. a FLAG domain, a Strep-tag domain and/or a poly-His domain.

Examples of specific fusion proteins of the invention are SEQ ID NOs:1, 19, and 20.

A further aspect of the present invention relates to a nucleic acid molecule encoding a fusion protein as described herein. The nucleic acid molecule may be a DNA molecule, e.g. a double-stranded or single-stranded DNA molecule, or an RNA molecule. The nucleic acid molecule may encode the fusion protein or a precursor thereof, e.g. a pro- or pre-pro-form of the fusion protein which may comprise a signal sequence or other heterologous amino acid portions for secretion or purification which are preferably located at the N- and/or C-terminus of the fusion protein. The heterologous amino acid portions may be linked to the first and/or second domain via a protease cleavage site, e.g. a Factor $X_a$, thrombin or IgA protease cleavage site.

Examples of specific nucleic acid sequences of the invention are SEQ ID Nos:2, 21, and 22.

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosal integration vector, etc. Examples of suitable expression control sequences and vectors are described for example by Sambrook et al. (1989) *Molecular Cloning, A Laboratory Manual*, Cold Spring Harbor Press, and Ausubel et al. (1989), *Current Protocols in Molecular Biology*, John Wiley & Sons or more recent editions thereof.

Various expression vector/host cell systems may be used to express the nucleic acid sequences encoding the fusion proteins of the present invention. Suitable host cells include, but are not limited to, prokaryotic cells such as bacteria, e.g. *E.*

*coli*, eukaryotic host cells such as yeast cells, insect cells, plant cells or animal cells, preferably mammalian cells and, more preferably, human cells.

Further, the invention relates to a non-human organism transformed or transfected with a nucleic acid molecule as described above. Such transgenic organisms may be generated by known methods of genetic transfer including homologous recombination.

The fusion protein, the respective nucleic acid encoding therefor, the transformed or transfected cell as well as the trimeric complexes or oligomers of the trimeric complexes, all as described herein may be used for pharmaceutical, diagnostic and/or research applications.

A further aspect of the present invention relates to a pharmaceutical or diagnostic composition comprising as an active agent at least one fusion protein, one respective nucleic acid encoding therefor, one transformed or transfected cell as well as one trimeric complexe or oligomer of the trimeric complexes, all as described herein.

At least one fusion protein, one respective nucleic acid encoding therefor, one transformed or transfected cell as well as one trimeric complexe or oligomer of the trimeric complexes, all as described herein may be used in therapy, e.g., in the prophylaxis and/or treatment of disorders caused by, associated with and/or accompanied by dysfunction of TNF cytokines, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of TNF cytokines" as used herein is to be understood as any function or expression of a TNF cytokine that deviates from the normal function or expression of a TNF cytokine, e.g., overexpression of the TNF gene or protein, reduced or abolished expression of the TNF cytokine gene or protein compared to the normal physiological expression level of said TNF cytokine, increased activity of the TNF cytokine, reduced or abolished activity of the TNF cytokine, increased binding of the TNF cytokine to any binding partners, e.g., to a receptor, particularly a TRAIL receptor or another cytokine molecule, reduced or abolished binding to any binding partner, e.g. to a receptor, particularly a TRAIL receptor or another cytokine molecule, compared to the normal physiological activity or binding of said TNF cytokine.

The composition may be administered as monotherapy or as combination therapy with further medicaments, e.g. cytostatic or chemotherapeutic agents, corticosteroids and/or antibiotics.

The fusion protein is administered to a subject in need thereof, particularly a human patient, in a sufficient dose for the treatment of the specific conditions by suitable means. For example, the fusion protein may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e.g. intraperitoneally, intramuscularly or intravenously or locally, e.g. intranasally, subcutaneously or intrathecally. Preferred is intravenous administration.

The dose of the fusion protein administered will of course be dependent on the subject to be treated, on the subject's weight, the type and severity of the disease, the manner of administration and the judgement of the prescribing physician. For the administration of fusion proteins, a daily dose of 0.001 to 100 mg/kg is suitable.

EXAMPLE

1. Manufacture of a Fusion Protein

In the following, the basic structure of the recombinant proteins of the invention is shown exemplified for the receptor binding domain of the human CD95 ligand.

1.1 Polypeptide Structure

A) Amino acids Met1-Gly20

IgKappa-signal peptide, assumed signal peptidase cleavage site between the amino acids Gly20 and Glu21

B) Amino acids Glu21-Leu160

Receptor binding domain of the human CD95 ligand (CD95L; amino acids 142-281 of SEQ ID NO:30))

C) Amino acids Gly161-Ser171

Flexible linker element providing a distance of up to 30 Å between CD95L and the trimerization domain.

D) Amino acids Gly172-Leu198

Trimerization domain of the bacteriophage T4-fibritin (amino acids 458-484 of SEQ ID NO:23)

E) Amino acids Ser199-Lys222

Flexible element with a 6×His-Streptag II motif

The resulting protein was designated hs95L-AT4.

```
                                                              (SEQ ID NO: 1)
  1  METDTLLLWV  LLLWVPGSTG  ELRKVAHLTG  KSNSRSMPLE  WEDTYGIVLL  SGVKYKKGGL

61  VINETGLYFV  YSKVYFRGQS  CNNLPLSHKV  YMRNSKYPQD  LVMMEGKMMS  YCTTGQMWAR

121  SSYLGAVFNL  TSADHLYVNV  SELSLVNFEE  SQTFFGLYKL  GSSGSSGSSG  SGYIPEAPRD

181  GQAYVRKDGE  WVLLSTFLSG  PSSSSSHHHH  HHSAWSHPQF  EK
```

1.2 Gene Cassette Encoding the Polypeptide

The synthetic gene may be optimized in view of its codon-usage for the expression in suitable host cells, e.g. insect cells or mammalian cells.

```
                                                   (SEQ ID NO: 2 and SEQ ID NO: 3)
       Cpo-I      Nco-I
  1  CGGTCCGAAA CCATGGAGACCGATACACTGCTCTTGTGGGTACTCTTGCTGTGGGTTCCG
  1                    M  E  T  D  T  L  L  L  W  V  L  L  L  W  V  P
                BshT-I
```

```
                                       -continued
 61 GGATCTACCGGTGAACTCCGTAAAGTCGCCCATCTGACAGGAAAGTCCAACTCCCGATCA
 17  G  S  T  G  E  L  R  K  V  A  H  L  T  G  K  S  N  S  R  S 121 ATGCCTCTTGAGTGGGAAGACACCTACGGAATCGTCCTGTTGAGCGGAGTGAAGTACAAG
 37  M  P  L  E  W  E  D  T  Y  G  I  V  L  L  S  G  V  K  Y  K 181 AAGGGTGGTCTGGTCATCAACGAGACAGGCTTGTACTTCGTGTACTCCAAGGTGTACTTC
 57  K  G  G  L  V  I  N  E  T  G  L  Y  F  V  Y  S  K  V  Y  F 241 CGTGGTCAATCGTGCAACAACCTTCCACTCTCACACAAGGTCTACATGCGTAACTCGAAG
 77  R  G  Q  S  C  N  N  L  P  L  S  H  K  V  Y  M  R  N  S  K 301 TATCCGCAGGATCTGGTGATGATGGAGGGCAAGATGATGAGCTACTGCACGACCGGACAG
 97  Y  P  Q  D  L  V  M  M  E  G  K  M  M  S  Y  C  T  T  G  Q 361 ATGTGGGCACGTAGCTCATACCTGGGTGCTGTCTTCAACCTGACCAGTGCAGACCACCTG
117  M  W  A  R  S  S  Y  L  G  A  V  F  N  L  T  S  A  D  H  L 421 TACGTGAACGTGTCCGAACTGTCGCTCGTGAACTTCGAGGAGAGCCAGACGTTCTTCGGT
137  Y  V  N  V  S  E  L  S  L  V  N  F  E  E  S  Q  T  F  F  G BamH-I              Xho-I
481 CTCTACAAGCTGGGATCCTCAGGATCGAGTGGCTCGAGTGGTTCTGGATACATCCCAGAA
157  L  Y  K  L  G  S  S  G  S  S  G  S  S  G  S  G  Y  I  P  E 541 GCACCCAGAGACGGTCAGGCTTATGTCCGCAAAGACGGAGAATGGGTTCTGCTCTCGACC
177  A  P  R  D  G  Q  A  Y  V  R  K  D  G  E  W  V  L  L  S  T Sac-I                            Eco47-III
601 TTCTTGTCGGGTCCGAGCTCAAGCTCATCTCATCATCATCATCATAGCGCTTGGTCT
197  F  L  S  G  P  S  S  S  S  H  H  H  H  H  H  S  A  W  S Oli-I            Not-I        Hind-III
661 CACCCGCAGTTCGAGAAATGACACCATAGTGATAAGTAGCGGCCGCAGTAAGCTT
217  H  P  Q  F  E  K  STOP
```

1.3 Cloning Strategy of hs95L-AT4

The synthetic gene is excised from the transfer plasmid by means of Cpo-I/Hind-III hydrolysis and cloned into a suitable vector.

The sequence coding for the C-terminal Streptag-II may be deleted, e.g. by simultaneous hydrolysis with the blunt-end cutters Eco47-III and Oli-I and religation of the vector. A stop codon is therefor introduced by the fusion of the restriction enzyme half-sites downstream of the 6×Histag:

A) 3' terminus of the cassette prior to hydrolysis with Eco47-III and Oli-I

```
                                           (SEQ ID NO: 4 and SEQ ID NO: 5)
Eco47-III          Oli-I            Not-I        Hind-III
AGCGCTTGGTCTCACCCGCAGTTCGAGAAATGACACCATAGTGATAAGTAGCGGCCGCAGTAAGCTT
 S  A  W  S  H  P  Q  F  E  K  STOP
```

B) 3' terminus of the cassette after hydrolysis and religation

```
                         (SEQ ID NO: 6)
               Not-I        Hind-III
  AGCTAGTGATAAGTAGCGGCCGCAGTAAGCTT
   S  STOP
```

Sequence of the synthetic gene:

```
                                          (SEQ ID NO: 7)
CGG TCC GAA ACC ATG GAG ACC GAT ACA CTG CTC TTG

TGG GTA CTC TTG CTG TGG GTT CCG GGA TCT ACC GGT

GAA CTC CGT AAA GTC GCC CAT CTG ACA GGA AAG TCC

AAC TCC CGA TCA ATG CCT CTT GAG TGG GAA GAC ACC

TAC GGA ATC GTC CTG TTG AGC GGA GTG AAG TAC AAG
```

```
                                          -continued
AAG GGT GGT CTG GTC ATC AAC GAG ACA GGC TTG TAC

TTC GTG TAC TCC AAG GTG TAC TTC CGT GGT CAA TCG

TGC AAC AAC CTT CCA CTC TCA CAC AAG GTC TAC ATG

CGT AAC TCG AAG TAT CCG CAG GAT CTG GTG ATG ATG

GAG GGC AAG ATG ATG AGC TAC TGC ACG ACC GGA CAG
```

```
                                          -continued
ATG TGG GCA CGT AGC TCA TAC CTG GGT GCT GTC TTC

AAC CTG ACC AGT GCA GAC CAC CTG TAC GTG AAC GTG

TCC GAA CTG TCG CTC GTG AAC TTC GAG GAG AGC CAG

ACG TTC TTC GGT CTC TAC AAG CTG GGA TCC TCA GGA

TCG AGT GGC TCG AGT GGT TCT GGA TAC ATC CCA GAA

GCA CCC AGA GAC GGT CAG GCT TAT GTC CGC AAA GAC

GGA GAA TGG GTT CTG CTC TCG ACC TTC TTG TCG GGT

CCG AGC TCA AGC TCA TCT CAT CAT CAT CAT CAT CAT

AGC GCT TGG TCT CAC CCG CAG TTC GAG AAA TGA CAC

CAT AGT GAT AAG TAG CGG CCG CAG TAA GCT T
```

2. Expression and Purification a) Cloning, Expression and Purification of hs95L-AT4

Hek 293T cells grown in DMEM+GlutaMAX (GibCo) supplemented with 10% FBS, 100 units/ml Penicillin and 100 µg/ml Streptomycin were transiently transfected with a plasmid containing an expression cassette for hs95L-AT4. Cell culture supernatant containing recombinant hs95L-AT4 was harvested three days post transfection and clarified by centrifugation at 300 g followed by filtration through a 0.22 µm sterile filter. For affinity purification Streptactin Sepharose was packed to a column (gel bed 1 ml), equilibrated with 15 ml buffer W (100 mM Tris-HCl, 150 mM NaCl pH 8.0) and the cell culture supernatant was applied to the column with a flow rate of 4 ml/min. Subsequently, the column was washed with 15 ml buffer W and bound hs95L-AT4 was eluted step-wise by addition of 7×1 ml buffer E (100 mM Tris HCl, 150 mM NaCl, 2.5 mM Desthiobiotin pH 8.0). The protein amount of the eluate fractions was quantified and peak fractions were concentrated by ultrafiltration and further purified by size exclusion chromatography (SEC).

Figure 1A:
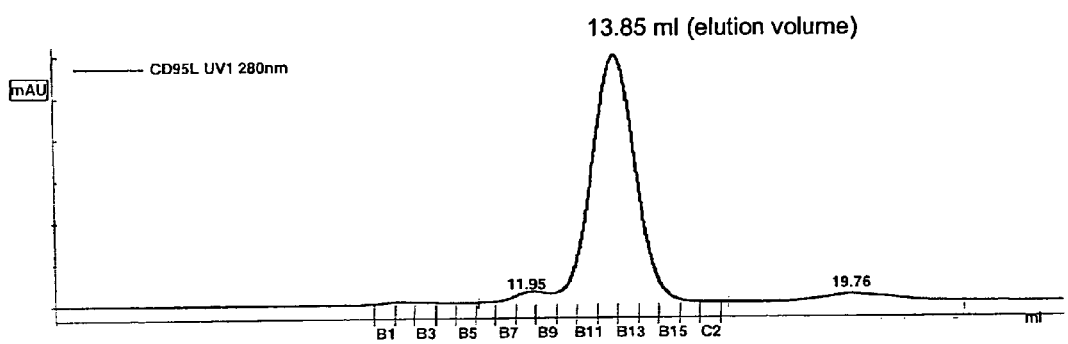
FIG. 1: A) SEC analysis of Streptactin affinity purified hs95L-AT4: Affinity purified protein eluted by desthiobiotin from immobilized Streptactin was loaded onto a Superdex200 column. The protein elution profile of the SEC run was measured at OD280. The retention volume of the respective hs95L-AT4 peak and the fraction numbers are indicated.
Figure 1B:
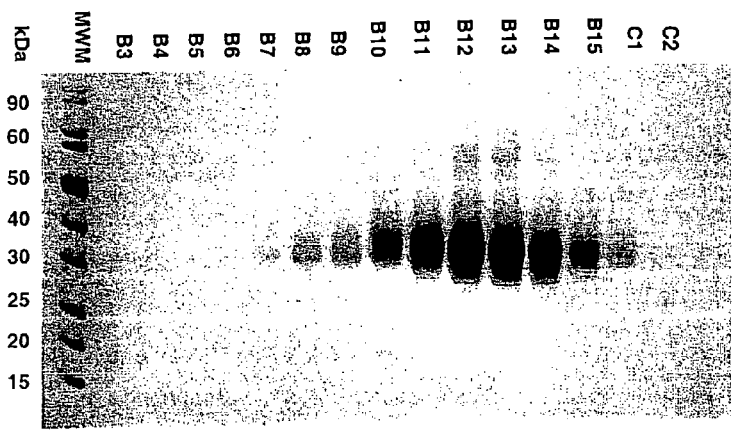

SEC was performed on a Superdex 200 column using an Äkta chromatography system (GE-Healthcare). The column was equilibrated with phosphate buffered saline and the concentrated, Streptactin purified hs95L-AT4 was loaded onto the SEC column at a flow rate of 0.5 ml/min. The elution profile of hs95L-AT4 monitored by absorbance at 280 nm showed a prominent protein peak at 13.85 ml (FIG. 1A). Peak fractions were subsequently analysed under denaturing conditions by SDS-PAGE and silver staining (FIG. 1B). Based on calibration with standard proteins hs95L-AT4 runs at about 30 KDa. The calculated theoretical molecular weight of hs95L-AT4 monomer is 22.4 KDa. The higher apparent molecular weight of about 30 KDa after SDS-PAGE is probably due to carbohydrate modifications of hs95L-AT4.

For determination of the apparent molecular weight of purified hs95L-AT4 under native conditions a Superdex 200 column was loaded with standard proteins of known molecular weight. Based on the elution volume of the standard proteins a calibration curve was calculated and the apparent molecular weight of purified hs95L-AT4 was determined to be 90.3 KDa indicating a stable trimeric structure of hs95L-AT4 (FIG. 2; Table 4).

b) Cloning, Expression and Purification of Human CD95L-A69 (hs95L-A69) and Human TRAIL-AT4 (hsTRAIL-AT4)

The amino acid sequence of the hs95L-A69- and hsTRAIL-AT4-constructs (SEQ ID NO:19 and SEQ ID NO:20) were backtranslated and their codon usage optimised for mammalian cell-based expression. Gene synthesis was done by ENTELECHON GmbH (Regensburg, Germany).

Finally, the hs95L-A69 and hsTRAIL-AT4-expression-cassettes (SEQ ID NO:21 and SEQ ID NO:22) were subcloned into pCDNA4-HisMax-backbone (INVITROGEN), using unique Hind-III- and Not-I-sites of the plasmid.

The hs95L-A69 and hsTRAIL-AT4 proteins were purified from tissue culture supernatants of Hek293T cells transiently transfected with plasmids encoding the respective cDNA-constructs, as described for hsCD95L-AT4 (see 2a). Briefly, the recombinant expressed proteins were first purified via Streptactin affinity chromatography. In a second step the affinity peak fractions were further purified and analysed via SEC (FIGS. 5A and 6A). To check the purity of the purified proteins, SEC fractions were subsequently analysed by SDS-PAGE and Silver staining (FIGS. 5B and 6B). Data from SEC were in addition used to determine the native apparent molecular weight of the respective proteins.

3. Apoptosis Assay

A cellular assay with a Jurkat A3 permanent T-cell line was used to determine the apoptosis inducing activity of different CD95-ligand (CD95L) constructs. Jurkat cells were grown in flasks with RPMI 1640-medium+GlutaMAX (GibCo) supplemented with 10% FBS, 100 units/ml Penicillin and 100 µg/ml Streptomycin. Prior to the assay, 100,000 cells were seeded per well into a 96-well microtiterplate. The addition of different concentrations of CD95L to the wells was followed by a 3 hour incubation at 37° C. Cells were lysed by adding lysis buffer (250 mM HEPES, 50 mM $MgCl_2$, 10 mM EGTA, 5% Triton-x-100, 100 mM DTT, 10 mM AEBSF, pH 7.5) and plates were put on ice for 30 minutes. Apoptosis is paralleled by an increased activity of Caspase 3 and Caspase 7. Hence, cleavage of the specific Caspase 3/7 substrate Ac-DEVD-AFC (Biomol) was used to determine the extent of apoptosis. In fact, Caspase activity correlates with the percentage of apoptotic cells determined morphologically after staining the cells with propidium iodide and Hoechst-33342. For the Caspase activity assay, 20 µl cell lysate was transferred to a black 96-well microtiterplate. After the addition of 80 µl buffer containing 50 mM HEPES, 1% Sucrose, 0.1% CHAPS, 50 µM Ac-DEVD-AFC, and 25 mM DTT, pH 7.5, the plate was transferred to a Tecan GeniosPro microtiterplate reader and the increase in fluorescence intensity was monitored (excitation wavelength 400 nm, emission wavelength 505 nm). Exemplarily, FIG. 3 demonstrates the induction of caspase activity of SEC fractions of the CD95 ligand hs95L-AT4 in this cellular apoptosis assay. The extent of caspase activity is well in line with the hs95L-AT4 content of SEC fractions as shown in FIGS. 1A and 1B.

A cellular assay with a Jurkat A3 permanent T-cell line was also used to determine the apoptosis inducing activity of hs95L-A69 and hsTRAIL-AT4. Jurkat cells (100,000 cells per well) were incubated with the ligands for 3 hours at 37° C. Cells were lysed and apoptosis induction was monitored by determination of cleavage of the specific Caspase 3/7 substrate Ac-DEVD-AFC.

Based on their apparent molecular weights both purified proteins, hs95L-A69, and hsTRAIL-T4, were expressed and purified as stable homotrimeric proteins that induced apoptosis on Jurkat cells. A summary comparing the apparent molecular weights determined by SDS-PAGE and SEC with the theoretical molecular weights calculated on basis of the primary amino acid sequence is shown in Table 4.

This apoptosis assay was also used for the determination of biological activity of APG101. APG101 is a fusion protein comprising the extracellular domain of the human CD95-receptor (the in vivo binding partner of CD95 ligand) with human Fc. APG101 antagonizes the apoptosis inducing effect of CD95L by binding to the ligand. Prior to the addition of CD95L to the Jurkat cells, CD95L at a constant concentration was incubated for 30 minutes at 37° C. with different concentrations of APG101. An example of the effect of APG101 is shown in FIG. 4. The CD95 ligand hs95L-AT4 induces caspase activity in a dose dependent manner, an effect which is abolished by APG101.

TABLE 1

| Approved Gene symbol | TNFSF-number | Synonyms | Accession | NH2-aa | COOH-aa | Length |
|---|---|---|---|---|---|---|
| LTA | TNFSF-1 | LTA | gi|6806893|ref|NP_000586.2| | Ser59 | Leu205 | 147aa |
|  |  |  |  | Thr60 | Leu205 | 146aa |
| TNF | TNFSF-2 | TNF-alpha | gi|25952111|ref|NP_000585.2| | Asp86 | Leu233 | 148aa |
| LTB | TNFSF-3 | LTB | gi|4505035|ref|NP_002332.1| | Asp82 | Gly244 | 163aa |
|  |  |  |  | Gly86 | Gly244 | 159aa |
| TNFSF4 | TNFSF-4 | OX40L/GP34 | gi|4507603|ref|NP_003317.1| | Val52 | Leu183 | 132aa |
|  |  |  |  | Arg55 | Leu183 | 129aa |
| CD40LG | TNFSF-5 | CD40L | gi|4557433|ref|NP_000065.1| | Asp117 | Leu261 | 150aa |
|  |  |  |  | Glu112 | Leu261 | 145aa |
| FASLG | TNFSF-6 | CD95L/APO-L/FAS-L | gi|4557329|ref|NP_000630.1| | Glu142 | Leu281 | 140aa |
|  |  |  |  | Arg144 | Leu281 | 138aa |
| TNFSF7 | TNFSF-7 | CD27L | gi|4507605|ref|NP_001243.1| | Glu51 | Pro193 | 143aa |
|  |  |  |  | Asp56 | Pro193 | 138aa |
| TNFSF8 | TNFSF-8 | CD30L | gi|4507607|ref|NP_001235.1| | Lys97 | Asp234 | 138aa |
|  |  |  |  | Ser98 | Asp234 | 137aa |
|  |  |  |  | Leu102 | Asp234 | 133aa |
| TNFSF9 | TNFSF-9 | 4-1BB/CD137L | gi|4507609|ref|NP_003802.1| | Asp86 | Glu254 | 169aa |
| TNFSF10 | TNFSF-10 | TRAIL | gi|4507593|ref|NP_003801.1| | Glu116 | Gly281 | 166aa |
|  |  |  |  | Gly118 | Gly281 | 164aa |
| TNFSF11 | TNFSF-11 | TRANCE/RANKL | gi|4507595|ref|NP_003692.1| | Glu161 | Asp317 | 157aa |
| TNFSF12 | TNFSF-12 | TWEAK/Apo-3 | gi|4507597|ref|NP_003800.1| | Ala103 | His249 | 147aa |
|  |  |  |  | Arg104 | His249 | 146aa |
|  |  |  |  | Arg105 | His249 | 145aa |
| TNFSF13 | TNFSF-13 | APRIL/TALL-2/TRDL-1 | gi|26051248|ref|NP_742085.1| | Lys112 | Leu247 | 136aa |
| TNFSF13 | TNFSF-13 | APRIL/TALL-2/TRDL-1 | gi|4507599|ref|NP_003799.1| | Lys112 | Leu250 | 139aa |
| TNFSF13B | TNFSF-13B | BAFF/Blys | gi|5730097|ref|NP_006564.1| | Glu140 | Leu285 | 146aa |
| TNFSF14 | TNFSF-14 | LIGHT | gi|25952144|ref|NP_003798.2| | Glu91 | Val240 | 150aa |
| TNFSF15 | TNFSF-15 | TL1A/VEGI | gi|23510445|ref|NP_005109.2| | Asp91 | Leu251 | 161aa |
|  |  |  |  | Asp93 | Leu251 | 159aa |
| TNFSF18 | TNFSF-18 | GITRL | gi|4827034|ref|NP_005083.1| | Glu52 | Ser177 | 126aa |
| EDA |  | EDA-A1 | gi|4503449|ref|NP_001390.1| | Glu245 | Ser391 | 147aa |
| EDA |  | EDA-A2 | gi|54112101|ref|NP_001005609.1| | Glu245 | Ser389 | 145aa |

TABLE 2 gi|2104653|emb|CAA31379.1|whisker antigen control protein (AA 1-487) [*Enterobacteria* phage T4].

gyipeaprdgqayvrkdgewvllstfl
(Gly458-Leu485)

Natural variants:
gi|32453655|ref|NP_861864.1| Wac fibritin neck whiskers [*Enterobacteria* phage RB69]
gi|22652096|gb|AAN03610.1|fibritin protein gpwac [phage AR1]

(SEQ ID NO: 8)
GYIPEAPRDGQAYVRKDGEWVLLSTFL T4-foldon (SEQ ID NO: 9)
GYIEDAPSDGKFYVRKDGAWVELPTA *Enterobacteria* phage RB69

(SEQ ID NO: 10)
GYIPEAPKDGQAYVRKDGEWVLLSTFL phage AR1

TABLE 3

T4 foldon

GYIPEAPRDGQAYVRKDGEWVLLSTFL

T4 foldon muteins

GYIPEAPRDGQAYVRKDGEWVLLSTFL

GYIPEAPRDGQAYVRRDGDWVLLSTFL (SEQ ID NO: 11)

GYIPEAPKDGQAYVRKDGEWVLLSTFL (SEQ ID NO: 12)

TABLE 3-continued

GYIPDAPRDGQAYVRKDGEWVLLSTFL (SEQ ID NO: 13)

GYIPEAPREGQAYVRKDGEWVLLSTFL (SEQ ID NO: 14)

GYIPEAPRDGQAYVRKDGEWVFLSTFL (SEQ ID NO: 15)

GYIPEAPRDGQAYVRKDGEWVLLSTFV (SEQ ID NO: 16)

GYIPEAPRDGQAYVRKDGEWVLLSTFI (SEQ ID NO: 17)

GYIPDAPREGQAYVRKDGEWVFLSTFV (SEQ ID NO: 18)

TABLE 4

Comparison of theoretical and experimental determined molecular weights

| Construct: | Theoretical MW of monomer (kDa) | Apparent MW based on SDS-PAGE (kDa) | Apparent MW based on SEC (kDa) | ELUTION volume (SEC in ml) |
|---|---|---|---|---|
| hsCD95L-AT4 | 22.4 | 30 | 90.3 | 13.85 |
| hsCD95L-A69 | 22.5 | 31 | 80 | 14.07 |
| hsTRAIL-AT4 | 25.3 | 25 | 61 | 14.56 |

The invention claimed is:

1. A fusion protein comprising:
   (i) a TNF-superfamily cytokine selected from the group consisting of CD95L or TRAIL, or a receptor binding domain thereof;
   (ii) a fibritin trimerization domain; and
   (iii) a flexible linker between (i) and (ii),
   wherein the fibritin trimerization domain is a bacteriophage RB69 trimerization domain, and the linker has 5-20 amino acid residues having the amino acid sequence $(GSS)_z(SSG)_b(GS)_c(S)_d$, a, b, c, d are independently 0, 1, 2, 3, 4, or 5.

2. The fusion protein according to claim 1, wherein the fibritin trimerization domain comprises amino acid residues 455-480 of SEQ ID NO:24, amino acid residues or 456-480 of SEQ ID NO:24.

3. The fusion protein according to claim 1, wherein the TNF-superfamily cytokine or receptor binding domain thereof is fused to the N-terminus of the linker and the linker is fused to the N-terminus of the fibritin trimerization domain.

4. The fusion protein according to claim 3, further comprising:
   (iv) a N-terminal signal peptide.

5. The fusion protein according to claim 4, further comprising:
   (v) a protease cleavage site C-terminal to the signal peptide.

6. The fusion protein according to claim 3, further comprising:
   (iv) a C-terminal flexible element.

7. The fusion protein according to claim 6, further comprising:
   (v) a recognition or purification domain fused in frame to the C-terminal flexible element.

8. The fusion protein according to claim 1, wherein the fibritin trimerization domain is fused to the N-terminus of the linker and the linker is fused to the N-terminus of the TNF-superfamily cytokine or receptor binding domain thereof.

9. The fusion protein according to claim 8, further comprising:
   (iv) a N-terminal signal peptide.

10. The fusion protein according to claim 9, further comprising:
    (v) a protease cleavage site C-terminal to the signal peptide.

11. The fusion protein according to claim 8, further comprising:
    (iv) a C-terminal flexible element.

12. The fusion protein according to claim 11, further comprising:
    (v) a recognition or purification domain fused in frame to the C-terminal flexible element.

13. The fusion protein according to claim 1, wherein the fusion protein forms a trimeric complex or an oligomer of a trimeric complex.

14. The fusion protein according to claim 13, wherein the complex consists of three identical fusion proteins.

15. The fusion protein according to claim 1, wherein said TNF-superfamily cytokine is CD95L.

16. The fusion protein according to claim 15, wherein said CD95L has the amino acid sequence of SEQ ID. NO: 30.

17. The fusion protein according to claim 15, wherein the CD95L comprises amino acid residues 142-281 or amino acid residues 144-281 of SEQ ID NO:30.

18. The fusion protein according to claim 1, wherein the TNF-superfamily cytokine is TRAIL, which comprises amino acid residues 116-281, amino acid residues 118-281, or amino acid residues 120-281 of SEQ ID NO:34.

19. The fusion protein according to claim 1, wherein the linker has a length of 6, 9, 12, 15 or 18 amino acid residues.

20. The fusion protein according to claim 1, wherein the linker has the amino acid sequence of GSS GSS GSS GS (SEQ ID NO: 46).

21. A pharmaceutical composition comprising:
    the fusion protein according to claim 1, and
    a pharmaceutically acceptable carrier, diluent or adjuvant.

22. A nucleic acid encoding the fusion protein according to claim 1.

23. An expression vector comprising the nucleic acid according to claim 22.

24. A cell transformed or transfected with the expression vector according to claim 23.

* * * * *

SEQUENCE LISTING

<160> NUMBER OF SEQ ID NOS: 47

<210> SEQ ID NO 1
<211> LENGTH: 222
<212> TYPE: PRT
<213> ORGANISM: Artificial Sequence
<220> FEATURE:
<223> OTHER INFORMATION: hs95L-AT4 fusion protein
<220> FEATURE:
<221> NAME/KEY: MISC_FEATURE
<222> LOCATION: (1)..(20)
<223> OTHER INFORMATION: IgKappa signal peptide
<220> FEATURE:
<221> NAME/KEY: MISC_FEATURE
<222> LOCATION: (21)..(160)
<223> OTHER INFORMATION: Receptor binding domain of human CD95L
<220> FEATURE:
<221> NAME/KEY: MISC_FEATURE
<222> LOCATION: (161)..(171)
<223> OTHER INFORMATION: Flexible linker
<220> FEATURE:
<221> NAME/KEY: MISC_FEATURE
<222> LOCATION: (172)..(198)
<223> OTHER INFORMATION: Trimerization (foldon) domain of bacteriophage
    T4 fibritin
<220> FEATURE:
<221> NAME/KEY: MISC_FEATURE
<222> LOCATION: (199)..(222)
<223> OTHER INFORMATION: Flexible linker with His-Streptag II motif

<400> SEQUENCE: 1

```
Met Glu Thr Asp Thr Leu Leu Leu Trp Val Leu Leu Trp Val Pro
1               5                   10                  15

Gly Ser Thr Gly Glu Leu Arg Lys Val Ala His Leu Thr Gly Lys Ser
            20                  25                  30

Asn Ser Arg Ser Met Pro Leu Glu Trp Glu Asp Thr Tyr Gly Ile Val
            35                  40                  45

Leu Leu Ser Gly Val Lys Tyr Lys Lys Gly Gly Leu Val Ile Asn Glu
        50                  55                  60

Thr Gly Leu Tyr Phe Val Tyr Ser Lys Val Tyr Phe Arg Gly Gln Ser
65                  70                  75                  80

Cys Asn Asn Leu Pro Leu Ser His Lys Val Tyr Met Arg Asn Ser Lys
                85                  90                  95

Tyr Pro Gln Asp Leu Val Met Met Glu Gly Lys Met Met Ser Tyr Cys
            100                 105                 110

Thr Thr Gly Gln Met Trp Ala Arg Ser Ser Tyr Leu Gly Ala Val Phe
            115                 120                 125

Asn Leu Thr Ser Ala Asp His Leu Tyr Val Asn Val Ser Glu Leu Ser
        130                 135                 140

Leu Val Asn Phe Glu Glu Ser Gln Thr Phe Phe Gly Leu Tyr Lys Leu
145                 150                 155                 160

Gly Ser Ser Gly Ser Ser Gly Ser Ser Gly Tyr Ile Pro Glu
                165                 170                 175

Ala Pro Arg Asp Gly Gln Ala Tyr Val Arg Lys Asp Gly Glu Trp Val
            180                 185                 190

Leu Leu Ser Thr Phe Leu Ser Gly Pro Ser Ser Ser Ser His His
        195                 200                 205

His His His Ser Ala Trp Ser His Pro Gln Phe Glu Lys
            210                 215                 220
```

<210> SEQ ID NO 2
<211> LENGTH: 715

```
<212> TYPE: DNA
<213> ORGANISM: Artificial Sequence
<220> FEATURE:
<223> OTHER INFORMATION: Codon optimized hs95L-AT4 expression cassette
<220> FEATURE:
<221> NAME/KEY: CDS
<222> LOCATION: (13)..(678)

<400> SEQUENCE: 2
cggtccgaaa cc atg gag acc gat aca ctg ctc ttg tgg gta ctc ttg ctg        51
              Met Glu Thr Asp Thr Leu Leu Leu Trp Val Leu Leu Leu
                1               5                  10 tgg gtt ccg gga tct acc ggt gaa ctc cgt aaa gtc gcc cat ctg aca          99
Trp Val Pro Gly Ser Thr Gly Glu Leu Arg Lys Val Ala His Leu Thr
 15                  20                  25 gga aag tcc aac tcc cga tca atg cct ctt gag tgg gaa gac acc tac         147
Gly Lys Ser Asn Ser Arg Ser Met Pro Leu Glu Trp Glu Asp Thr Tyr
 30                  35                  40                  45 gga atc gtc ctg ttg agc gga gtg aag tac aag aag ggt ggt ctg gtc         195
Gly Ile Val Leu Leu Ser Gly Val Lys Tyr Lys Lys Gly Gly Leu Val
                 50                  55                  60 atc aac gag aca ggc ttg tac ttc gtg tac tcc aag gtg tac ttc cgt         243
Ile Asn Glu Thr Gly Leu Tyr Phe Val Tyr Ser Lys Val Tyr Phe Arg
             65                  70                  75 ggt caa tcg tgc aac aac ctt cca ctc tca cac aag gtc tac atg cgt         291
Gly Gln Ser Cys Asn Asn Leu Pro Leu Ser His Lys Val Tyr Met Arg
         80                  85                  90 aac tcg aag tat ccg cag gat ctg gtg atg atg gag ggc aag atg atg         339
Asn Ser Lys Tyr Pro Gln Asp Leu Val Met Met Glu Gly Lys Met Met
     95                 100                 105 agc tac tgc acg acc gga cag atg tgg gca cgt agc tca tac ctg ggt         387
Ser Tyr Cys Thr Thr Gly Gln Met Trp Ala Arg Ser Ser Tyr Leu Gly
110                 115                 120                 125 gct gtc ttc aac ctg acc agt gca gac cac ctg tac gtg aac gtg tcc         435
Ala Val Phe Asn Leu Thr Ser Ala Asp His Leu Tyr Val Asn Val Ser
                130                 135                 140 gaa ctg tcg ctc gtg aac ttc gag gag agc cag acg ttc ttc ggt ctc         483
Glu Leu Ser Leu Val Asn Phe Glu Glu Ser Gln Thr Phe Phe Gly Leu
            145                 150                 155 tac aag ctg gga tcc tca gga tcg agt ggc tcg agt ggt tct gga tac         531
Tyr Lys Leu Gly Ser Ser Gly Ser Ser Gly Ser Ser Gly Ser Gly Tyr
        160                 165                 170 atc cca gaa gca ccc aga gac ggt cag gct tat gtc cgc aaa gac gga         579
Ile Pro Glu Ala Pro Arg Asp Gly Gln Ala Tyr Val Arg Lys Asp Gly
    175                 180                 185 gaa tgg gtt ctg ctc tcg acc ttc ttg tcg ggt ccg agc tca agc tca         627
Glu Trp Val Leu Leu Ser Thr Phe Leu Ser Gly Pro Ser Ser Ser Ser
190                 195                 200                 205 tct cat cat cat cat cat cat agc gct tgg tct cac ccg cag ttc gag         675
Ser His His His His His His Ser Ala Trp Ser His Pro Gln Phe Glu
                210                 215                 220 aaa tgacaccata gtgataagta gcggccgcag taagctt                            715
Lys

<210> SEQ ID NO 3
<211> LENGTH: 222
<212> TYPE: PRT
<213> ORGANISM: Artificial Sequence
<220> FEATURE:
<223> OTHER INFORMATION: Synthetic Construct

<400> SEQUENCE: 3

Met Glu Thr Asp Thr Leu Leu Leu Trp Val Leu Leu Leu Trp Val Pro
```

-continued

```
                  1               5              10              15

Gly Ser Thr Gly Glu Leu Arg Lys Val Ala His Leu Thr Gly Lys Ser
                        20                  25                  30

Asn Ser Arg Ser Met Pro Leu Glu Trp Glu Asp Thr Tyr Gly Ile Val
                        35                  40                  45

Leu Leu Ser Gly Val Lys Tyr Lys Gly Gly Leu Val Ile Asn Glu
                    50                  55                  60

Thr Gly Leu Tyr Phe Val Tyr Ser Lys Val Tyr Phe Arg Gly Gln Ser
         65                  70                  75                  80

Cys Asn Asn Leu Pro Leu Ser His Lys Val Tyr Met Arg Asn Ser Lys
                            85                  90                  95

Tyr Pro Gln Asp Leu Val Met Met Glu Gly Lys Met Met Ser Tyr Cys
                       100                 105                 110

Thr Thr Gly Gln Met Trp Ala Arg Ser Ser Tyr Leu Gly Ala Val Phe
                       115                 120                 125

Asn Leu Thr Ser Ala Asp His Leu Tyr Val Asn Val Ser Glu Leu Ser
                       130                 135                 140

Leu Val Asn Phe Glu Glu Ser Gln Thr Phe Phe Gly Leu Tyr Lys Leu
        145                 150                 155                 160

Gly Ser Ser Gly Ser Ser Gly Ser Ser Gly Ser Gly Tyr Ile Pro Glu
                       165                 170                 175

Ala Pro Arg Asp Gly Gln Ala Tyr Val Arg Lys Asp Gly Glu Trp Val
                       180                 185                 190

Leu Leu Ser Thr Phe Leu Ser Gly Pro Ser Ser Ser Ser His His
                       195                 200                 205

His His His His Ser Ala Trp Ser His Pro Gln Phe Glu Lys
                       210                 215                 220

<210> SEQ ID NO 4
<211> LENGTH: 50
<212> TYPE: DNA
<213> ORGANISM: Artificial Sequence
<220> FEATURE:
<223> OTHER INFORMATION: 3' terminus of hs95L-AT4 expression cassette
      prior to hydrolysis
<220> FEATURE:
<221> NAME/KEY: CDS
<222> LOCATION: (1)..(30)

<400> SEQUENCE: 4 agc gct tgg tct cac ccg cag ttc gag aaa tgacaccata gtgataagta            50
Ser Ala Trp Ser His Pro Gln Phe Glu Lys
  1               5                  10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Ser Ala Trp Ser His Pro Gln Phe Glu Lys
  1               5                  10

<210> SEQ ID NO 6
<211> LENGTH: 32
<212> TYPE: DNA
<213> ORGANISM: Artificial Sequence
<220> FEATURE:
<223> OTHER INFORMATION: 3' terminus of hs95L-AT4 expression cassette
      after hydrolysis and re-ligation
```

```
<220> FEATURE:
<221> NAME/KEY: CDS
<222> LOCATION: (1)..(3)

<400> SEQUENCE: 6 agc tagtgataag tagcggccgc agtaagctt                                   32
Ser
1

<210> SEQ ID NO 7
<211> LENGTH: 715
<212> TYPE: DNA
<213> ORGANISM: Artificial Sequence
<220> FEATURE:
<223> OTHER INFORMATION: Codon-optimized hs95L-AT4 expression cassette
      after 3' hydrolysis and re-ligation

<400> SEQUENCE: 7
cggtccgaaa ccatggagac cgatacactg ctcttgtggg tactcttgct gtgggttccg      60
ggatctaccg gtgaactccg taaagtcgcc catctgacag aaagtccaa ctcccgatca     120
atgcctcttg agtgggaaga cacctacgga atcgtcctgt tgagcggagt gaagtacaag     180
aagggtggtc tggtcatcaa cgagacaggc ttgtacttcg tgtactccaa ggtgtacttc     240
cgtggtcaat cgtgcaacaa ccttccactc tcacacaagg tctacatgcg taactcgaag     300
tatccgcagg atctggtgat gatggagggc aagatgatga ctactgcac gaccggacag     360
atgtgggcac gtagctcata cctgggtgct gtcttcaacc tgaccagtgc agaccacctg     420
tacgtgaacg tgtccgaact gtcgctcgtg aacttcgagg agagccagac gttcttcggt     480
ctctacaagc tgggatcctc aggatcgagt ggctcgagtg gttctggata catcccagaa     540
gcacccagag acggtcaggc ttatgtccgc aaagacggag aatgggttct gctctcgacc     600
ttcttgtcgg gtccgagctc aagctcatct catcatcatc atcatcatag cgcttggtct     660
cacccgcagt tcgagaaatg acaccatagt gataagtagc ggccgcagta agctt         715

<210> SEQ ID NO 8
<211> LENGTH: 27
<212> TYPE: PRT
<213> ORGANISM: Bacteriophage T4

<400> SEQUENCE: 8

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 9
<211> LENGTH: 26
<212> TYPE: PRT
<213> ORGANISM: Bacteriophage RB69

<400> SEQUENCE: 9

Gly Tyr Ile Glu Asp Ala Pro Ser Asp Gly Lys Phe Tyr Val Arg Lys
1               5                   10                  15

Asp Gly Ala Trp Val Glu Leu Pro Thr Ala
            20                  25

<210> SEQ ID NO 10
<211> LENGTH: 27
<212> TYPE: PRT
<213> ORGANISM: Bacteriophage AR1

<400> SEQUENCE: 10
```

Gly Tyr Ile Pro Glu Ala Pro Lys Asp Gly Gln Ala Tyr Val Arg Lys
1               5                   10                  15

Asp Gly Glu Trp Val Leu Leu Ser Thr Phe Leu
            20                  25

<210> SEQ ID NO 11
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 11

Gly Tyr Ile Pro Glu Ala Pro Arg Asp Gly Gln Ala Tyr Val Arg Arg
1               5                   10                  15

Asp Gly Asp Trp Val Leu Leu Ser Thr Phe Leu
            20                  25

<210> SEQ ID NO 12
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 12

Gly Tyr Ile Pro Glu Ala Pro Lys Asp Gly Gln Ala Tyr Val Arg Lys
1               5                   10                  15

Asp Gly Glu Trp Val Leu Leu Ser Thr Phe Leu
            20                  25

<210> SEQ ID NO 13
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 13

Gly Tyr Ile Pro Asp Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 14
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 14

Gly Tyr Ile Pro Glu Ala Pro Arg Glu Gly Gln Ala Tyr Val Arg Lys
1               5                   10                  15

Asp Gly Glu Trp Val Leu Leu Ser Thr Phe Leu
            20                  25

<210> SEQ ID NO 15
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 15

```
Gly Tyr Ile Pro Glu Ala Pro Arg Asp Gly Gln Ala Tyr Val Arg Lys
1               5                   10                  15

Asp Gly Glu Trp Val Phe Leu Ser Thr Phe Leu
            20                  25

<210> SEQ ID NO 16
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 16

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Val
            20                  25

<210> SEQ ID NO 17
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 17

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Ile
            20                  25

<210> SEQ ID NO 18
<211> LENGTH: 27
<212> TYPE: PRT
<213> ORGANISM: Artificial Sequence
<220> FEATURE:
<223> OTHER INFORMATION: Mutein of T4 foldon

<400> SEQUENCE: 18

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Val
            20                  25

<210> SEQ ID NO 19
<211> LENGTH: 221
<212> TYPE: PRT
<213> ORGANISM: Artificial Sequence
<220> FEATURE:
<223> OTHER INFORMATION: hs95L-A69 fusion protein
<220> FEATURE:
<221> NAME/KEY: MISC_FEATURE
<222> LOCATION: (161)..(171)
<223> OTHER INFORMATION: Linker

<400> SEQUENCE: 19

Met Glu Thr Asp Thr Leu Leu Leu Trp Val Leu Leu Leu Trp Val Pro
1               5                   10                  15

Gly Ser Thr Gly Glu Leu Arg Lys Val Ala His Leu Thr Gly Lys Ser
            20                  25                  30

Asn Ser Arg Ser Met Pro Leu Glu Trp Glu Asp Thr Tyr Gly Ile Val
        35                  40                  45

Leu Leu Ser Gly Val Lys Tyr Lys Lys Gly Gly Leu Val Ile Asn Glu
    50                  55                  60
```

```
Thr Gly Leu Tyr Phe Val Tyr Ser Lys Val Tyr Phe Arg Gly Gln Ser
 65                  70                  75                  80

Cys Asn Asn Leu Pro Leu Ser His Lys Val Tyr Met Arg Asn Ser Lys
                 85                  90                  95

Tyr Pro Gln Asp Leu Val Met Met Glu Gly Lys Met Met Ser Tyr Cys
            100                 105                 110

Thr Thr Gly Gln Met Trp Ala Arg Ser Ser Tyr Leu Gly Ala Val Phe
            115                 120                 125

Asn Leu Thr Ser Ala Asp His Leu Tyr Val Asn Val Ser Glu Leu Ser
        130                 135                 140

Leu Val Asn Phe Glu Glu Ser Gln Thr Phe Phe Gly Leu Tyr Lys Leu
145                 150                 155                 160

Gly Ser Ser Gly Ser Gly Ser Ser Gly Ser Gly Tyr Ile Glu Asp
                165                 170                 175

Ala Pro Ser Asp Gly Lys Phe Tyr Val Arg Lys Asp Gly Ala Trp Val
            180                 185                 190

Glu Leu Pro Thr Ala Ser Gly Pro Ser Ser Ser Ser His His His
            195                 200                 205

His His His Ser Ala Trp Ser His Pro Gln Phe Glu Lys
        210                 215                 220

<210> SEQ ID NO 20
<211> LENGTH: 243
<212> TYPE: PRT
<213> ORGANISM: Artificial Sequence
<220> FEATURE:
<223> OTHER INFORMATION: hsTRAIL-AT4 fusion protein
<220> FEATURE:
<221> NAME/KEY: MISC_FEATURE
<222> LOCATION: (182)..(192)
<223> OTHER INFORMATION: Linker

<400> SEQUENCE: 20

Met Glu Thr Asp Thr Leu Leu Leu Trp Val Leu Leu Leu Trp Val Pro
 1               5                  10                  15

Ala Gly Asn Gly Gln Arg Val Ala Ala His Ile Thr Gly Thr Arg Gly
                20                  25                  30

Arg Ser Asn Thr Leu Ser Ser Pro Asn Ser Lys Asn Glu Lys Ala Leu
            35                  40                  45

Gly Arg Lys Ile Asn Ser Trp Glu Ser Ser Arg Ser Gly His Ser Phe
        50                  55                  60

Leu Ser Asn Leu His Leu Arg Asn Gly Glu Leu Val Ile His Glu Lys
 65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
            180                 185                 190
```

Gly Tyr Ile Pro Glu Ala Pro Arg Asp Gly Gln Ala Tyr Val Arg Lys
            195                 200                 205

Asp Gly Glu Trp Val Leu Leu Ser Thr Phe Leu Ser Gly Pro Ser Ser
        210                 215                 220

Ser Ser Ser His His His His His His Ser Ala Trp Ser His Pro Gln
225                 230                 235                 240

Phe Glu Lys

<210> SEQ ID NO 21
<211> LENGTH: 706
<212> TYPE: DNA
<213> ORGANISM: Artificial Sequence
<220> FEATURE:
<223> OTHER INFORMATION: Codon-optimized hs95L-A69 expression cassette

<400> SEQUENCE: 21
aagcttgccg ccaccatgga gaccgataca ctgctcttgt gggtactctt gctgtgggtt       60
ccgggatcta ccggtgaact ccgtaaagtc gcccatctga caggaaagtc caactcccga      120
tcaatgcctc ttgagtggga agacacctac ggaatcgtcc tgttgagcgg agtgaagtac      180
aagaagggtg gtctggtcat caacgagaca ggcttgtact tcgtgtactc caaggtgtac      240
ttccgtggtc aatcgtgcaa caaccttcca ctctcacaca aggtctacat gcgtaactcg      300
aagtatccgc aggatctggt gatgatggag ggcaagatga tgagctactg cacgaccgga      360
cagatgtggg cacgtagctc ataccctggg gctgtcttca acctgaccag tgcagaccac      420
ctgtacgtga acgtgtccga actgtcgctc gtgaacttcg aggagagcca gacgttcttc      480
ggtctctaca gctgggatc ctcaggaagc agtggctcaa gtggttctgg atatatcgaa      540
gatgctcctt cagacggtaa attctatgtt cgtaaagatg gtgcttgggt tgaacttcct      600
acagcttcag gtccgagctc aagctcatct catcatcatc atcatcatag cgcttggtct      660
cacccgcagt tcgagaaatg acaccatagt gataagtagc ggccgc                     706

<210> SEQ ID NO 22
<211> LENGTH: 772
<212> TYPE: DNA
<213> ORGANISM: Artificial Sequence
<220> FEATURE:
<223> OTHER INFORMATION: Codon-optimized hsTRAIL-AT4 expression cassette

<400> SEQUENCE: 22
aagcttgccg ccaccatgga gaccgataca ctgctcttgt gggtgctctt gctgtgggtt       60
cctgcaggta atggtcaaag agtcgcagct cacatcactg gactagagg caggagtaac      120
accctgagtt ctcccaattc aagaacgag aaagccctgg gtaggaagat caactcctgg      180
gaaagctcca gaagcggcca tagctttctt agcaacctcc acttgaggaa tggcgaactt      240
gtgatccatg agaagggctt ctactacatc tacagccaga cgtacttcag gttccaggag      300
gaaatcaagg agaacaccaa gaacgacaag cagatggtgc aatacatcta caagtacacg      360
tcatacccctg atcctatact gctgatgaag tccgccagaa acagttgctg gagcaaagac      420
gctgaatacg gcctgtattc catctatcag ggcggtatct ttgaactcaa ggagaacgac      480
aggatcttcg tgtctgtgac aaacgagcat ctgatcgaca tggaccatga gcgtctttc      540
ttcggtgcct tcttggtggg atcctcagga tcgagtggct cgagtggttc tggatacatc      600
ccagaagcac ccagagacgg tcaggcttat gtccgcaaag acggagaatg ggttctgctc      660
tcgaccttct tgtcgggtcc gagctcaagc tcatctcatc atcatcatca tcatagcgct      720
tggtctcacc cgcagttcga gaaatgacac catagtgata agtagcggcc gc                    772

<210> SEQ ID NO 23
<211> LENGTH: 487
<212> TYPE: PRT
<213> ORGANISM: Bacteriophage T4
<220> FEATURE:
<221> NAME/KEY: MISC_FEATURE
<222> LOCATION: (458)..(484)
<223> OTHER INFORMATION: Trimerization (foldon) domain

<400> SEQUENCE: 23

```
Met Thr Asp Ile Val Leu Asn Asp Leu Pro Phe Val Asp Gly Pro Pro
1               5                   10                  15

Ala Glu Gly Gln Ser Arg Ile Ser Trp Ile Lys Asn Gly Glu Glu Ile
                20                  25                  30

Leu Gly Ala Asp Thr Gln Tyr Gly Ser Glu Gly Ser Met Asn Arg Pro
            35                  40                  45

Thr Val Ser Val Leu Arg Asn Val Glu Val Leu Asp Lys Asn Ile Gly
        50                  55                  60

Ile Leu Lys Thr Ser Leu Glu Thr Ala Asn Ser Asp Ile Lys Thr Ile
65                  70                  75                  80

Gln Gly Ile Leu Asp Val Ser Gly Asp Ile Glu Ala Leu Ala Gln Ile
                85                  90                  95

Gly Ile Asn Lys Lys Asp Ile Ser Asp Leu Lys Thr Leu Thr Ser Glu
            100                 105                 110

His Thr Glu Ile Leu Asn Gly Thr Asn Asn Thr Val Asp Ser Ile Leu
        115                 120                 125

Ala Asp Ile Gly Pro Phe Asn Ala Glu Ala Asn Ser Val Tyr Arg Thr
130                 135                 140

Ile Arg Asn Asp Leu Leu Trp Ile Lys Arg Glu Leu Gly Gln Tyr Thr
                145                 150                 155                 160

Gly Gln Asp Ile Asn Gly Leu Pro Val Val Gly Asn Pro Ser Ser Gly
            165                 170                 175

Met Lys His Arg Ile Ile Asn Asn Thr Asp Val Ile Thr Ser Gln Gly
        180                 185                 190

Ile Arg Leu Ser Glu Leu Glu Thr Lys Phe Ile Glu Ser Asp Val Gly
    195                 200                 205

Ser Leu Thr Ile Glu Val Gly Asn Leu Arg Glu Glu Leu Gly Pro Lys
210                 215                 220

Pro Pro Ser Phe Ser Gln Asn Val Tyr Ser Arg Leu Asn Glu Ile Asp
225                 230                 235                 240

Thr Lys Gln Thr Thr Val Glu Ser Asp Ile Ser Ala Ile Lys Thr Ser
            245                 250                 255

Ile Gly Tyr Pro Gly Asn Asn Ser Ile Ile Thr Ser Val Asn Thr Asn
        260                 265                 270

Thr Asp Asn Ile Ala Ser Ile Asn Leu Glu Leu Asn Gln Ser Gly Gly
    275                 280                 285

Ile Lys Gln Arg Leu Thr Val Ile Glu Thr Ser Ile Gly Ser Asp Asp
290                 295                 300

Ile Pro Ser Ser Ile Lys Gly Gln Ile Lys Asp Asn Thr Thr Ser Ile
305                 310                 315                 320

Glu Ser Leu Asn Gly Ile Val Gly Glu Asn Thr Ser Ser Gly Leu Arg
                325                 330                 335

Ala Asn Val Ser Trp Leu Asn Gln Ile Val Gly Thr Asp Ser Ser Gly
            340                 345                 350
```

```
Gly Gln Pro Ser Pro His Gly Ser Leu Leu Asn Arg Val Ser Thr Ile
            355                 360                 365
Glu Thr Ser Val Ser Gly Leu Asn Asn Ala Val Gln Asn Leu Gln Val
        370                 375                 380
Glu Ile Gly Asn Asn Ser Ala Gly Ile Lys Gly Gln Val Val Ala Leu
385                 390                 395                 400
Asn Thr Leu Val Asn Gly Thr Asn Pro Asn Gly Ser Thr Val Glu Glu
                405                 410                 415
Arg Gly Leu Thr Asn Ser Ile Lys Ala Asn Glu Thr Asn Ile Ala Ser
            420                 425                 430
Val Thr Gln Glu Val Asn Thr Ala Lys Gly Asn Ile Ser Ser Leu Gln
        435                 440                 445
Gly Asp Val Gln Ala Leu Gln Glu Ala Gly Tyr Ile Pro Glu Ala Pro
    450                 455                 460
Arg Asp Gly Gln Ala Tyr Val Arg Lys Asp Gly Glu Trp Val Leu Leu
465                 470                 475                 480
Ser Thr Phe Leu Ser Pro Ala
                485

<210> SEQ ID NO 24
<211> LENGTH: 480
<212> TYPE: PRT
<213> ORGANISM: Bacteriophage RB69
<220> FEATURE:
<221> NAME/KEY: MISC_FEATURE
<222> LOCATION: (455)..(480)
<223> OTHER INFORMATION: Trimerization domain

<400> SEQUENCE: 24

Met Ile Glu Leu Lys Ser Leu Pro Tyr Val Asp Gly Pro Pro Asp Glu
1               5                   10                  15
Gly Gln Lys Arg Leu Asn Trp Ile Lys Asn Ser Glu Glu Ile Thr Gly
            20                  25                  30
Ala Asp Thr Leu Tyr Gly Ser Glu Gly Val Met Asn Arg Pro Ile Thr
        35                  40                  45
Glu Val Gln Arg Asn Val Glu Thr Ile Asn Asp Asn Val Lys Thr Ile
    50                  55                  60
Ala Glu Ser Leu Asp Thr Ala Asn Ala Asp Ile Val Thr Ile Lys Ser
65                  70                  75                  80
Ile Leu Asp Val Ser Gly Asp Val Asp Ala Leu Ala Gln Ile Gly His
                85                  90                  95
Asn Thr Asp Asp Ile Glu Val Leu Lys His Thr Val Asn Ser His Gly
            100                 105                 110
Val Asp Ile Leu Asn Thr Glu Glu Lys Leu Asp Asp Thr Ile Ala Asn
        115                 120                 125
Ile Gly Val Val Asn Pro Glu Thr Asp Ser Val Tyr Arg Thr Val Arg
    130                 135                 140
Asn Asp Leu Leu Trp Ile Lys Thr Glu Leu Gly Gln Tyr Thr Gly Gln
145                 150                 155                 160
Asp Ile Asn Gly Val Pro Thr Glu Gly Asn Glu Ser Thr Gly Met Lys
                165                 170                 175
Arg Arg Ile Ile Thr Asn Ser Ser Val Leu Val Asp Gln Gly Val Arg
            180                 185                 190
Leu Thr Glu Leu Glu Asn Lys Phe Ala Asp Ser Asp Val Gly Ala Leu
        195                 200                 205
Thr Thr Glu Val Glu Asn Leu Arg Gln Glu Ile Gly Pro Arg Pro Ser
    210                 215                 220
```

```
Leu Thr Val Pro Val Tyr Thr Arg Leu Ser Gly Ile Asp Ser Ser Ile
225                 230                 235                 240

Ser Ile Gln Thr Arg Asp Ile Ala Ala Leu Lys Asp Phe Val Gly Tyr
            245                 250                 255

Pro Asn Ser Thr Ala Ile Lys Thr Gln Val Glu Ala Asn Arg Leu Ser
            260                 265                 270

Ile Ser Thr Ile Asn Ser Asp Ile Asn Ser Pro Gly Gly Ile Lys Pro
        275                 280                 285

Arg Leu Thr Thr Leu Glu Thr Thr Ile Gly Ser Pro Asp Leu Pro Thr
    290                 295                 300

Thr Leu Gln Gly Lys Ile Lys Leu Asn Thr Asp Ser Ile Ser Gly Ile
305                 310                 315                 320

Asn Thr Val Leu Gly Val Asp Ser Ser Gly Leu Arg Phe Asn Val
                325                 330                 335

Ala Trp Leu Asn Gln Val Val Gly Val Asp Ser Asn Gly Gly Gln Pro
            340                 345                 350

Glu Pro Ala Gly Ser Leu Leu Tyr Arg Thr Arg Ile Leu Glu Thr Gly
        355                 360                 365

Val Thr Asp Leu Gly Asn Asn Ile Gln Asn Val Gln Thr Glu Leu Gly
    370                 375                 380

Thr Asn Ser Ser Gly Ile Lys Gly Gln Val Thr Ser Leu Asn Lys Leu
385                 390                 395                 400

Ile Ser Gly Thr Asn Pro Asn Gly Gln Thr Ile Glu Glu Arg Gly Ile
                405                 410                 415

Leu Pro Thr Val Lys Asn His Asp Thr Ser Ile Met Ala Leu Thr Thr
            420                 425                 430

Arg Val Thr Thr Leu Glu Thr Asp Leu Ala Ala Glu Ala Glu Ile
        435                 440                 445

Gln Ala Leu Lys Glu Ala Gly Tyr Ile Glu Asp Ala Pro Ser Asp Gly
    450                 455                 460

Lys Phe Tyr Val Arg Lys Asp Gly Ala Trp Val Glu Leu Pro Thr Ala
465                 470                 475                 480

<210> SEQ ID NO 25
<211> LENGTH: 205
<212> TYPE: PRT
<213> ORGANISM: Homo sapiens
<220> FEATURE:
<221> NAME/KEY: MISC_FEATURE
<222> LOCATION: (59)..(205)
<223> OTHER INFORMATION: Preferred receptor binding domain
<220> FEATURE:
<221> NAME/KEY: MISC_FEATURE
<222> LOCATION: (60)..(205)
<223> OTHER INFORMATION: Preferred receptor binding domain

<400> SEQUENCE: 25

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80
```

```
Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 26
<211> LENGTH: 233
<212> TYPE: PRT
<213> ORGANISM: Homo sapiens
<220> FEATURE:
<221> NAME/KEY: MISC_FEATURE
<222> LOCATION: (86)..(233)
<223> OTHER INFORMATION: Preferred receptor binding domain

<400> SEQUENCE: 26

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 27
<211> LENGTH: 244
<212> TYPE: PRT
<213> ORGANISM: Homo sapiens
<220> FEATURE:
<221> NAME/KEY: MISC_FEATURE
<222> LOCATION: (82)..(244)
<223> OTHER INFORMATION: Preferred receptor binding domain
<220> FEATURE:
<221> NAME/KEY: MISC_FEATURE
<222> LOCATION: (86)..(244)
<223> OTHER INFORMATION: Preferred receptor binding domain

<400> SEQUENCE: 27

```
Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
                20                  25                  30

Leu Leu Ala Val Pro Ile Thr Val Leu Ala Val Leu Ala Leu Val Pro
            35                  40                  45

Gln Asp Gln Gly Gly Leu Val Thr Glu Thr Ala Asp Pro Gly Ala Gln
50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly
```

<210> SEQ ID NO 28
<211> LENGTH: 183
<212> TYPE: PRT
<213> ORGANISM: Homo sapiens
<220> FEATURE:
<221> NAME/KEY: MISC_FEATURE
<222> LOCATION: (52)..(183)
<223> OTHER INFORMATION: Preferred receptor binding domain
<220> FEATURE:
<221> NAME/KEY: MISC_FEATURE
<222> LOCATION: (55)..(183)
<223> OTHER INFORMATION: Preferred receptor binding domain

<400> SEQUENCE: 28

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 29
<211> LENGTH: 261
<212> TYPE: PRT
<213> ORGANISM: Homo sapiens
<220> FEATURE:
<221> NAME/KEY: MISC_FEATURE
<222> LOCATION: (112)..(261)
<223> OTHER INFORMATION: Preferred receptor binding domain
<220> FEATURE:
<221> NAME/KEY: MISC_FEATURE
<222> LOCATION: (117)..(261)
<223> OTHER INFORMATION: Preferred receptor binding domain

<400> SEQUENCE: 29

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
```

```
                145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
                180                 185                 190
Leu Cys Leu Lys Ser Pro Gly Arg Phe Glu Arg Ile Leu Leu Arg Ala
                195                 200                 205
Ala Asn Thr His Ser Ser Ala Lys Pro Cys Gly Gln Gln Ser Ile His
                210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
                245                 250                 255
Gly Leu Leu Lys Leu
                260

<210> SEQ ID NO 30
<211> LENGTH: 281
<212> TYPE: PRT
<213> ORGANISM: Homo sapiens

<400> SEQUENCE: 30

Met Gln Gln Pro Phe Asn Tyr Pro Tyr Pro Gln Ile Tyr Trp Val Asp
1               5                   10                  15
Ser Ser Ala Ser Ser Pro Trp Ala Pro Pro Gly Thr Val Leu Pro Cys
                20                  25                  30
Pro Thr Ser Val Pro Arg Arg Pro Gly Gln Arg Arg Pro Pro Pro Pro
                35                  40                  45
Pro Pro Pro Pro Leu Pro Pro Pro Pro Pro Pro Leu Pro
                50                  55                  60
Pro Leu Pro Leu Pro Pro Leu Lys Lys Arg Gly Asn His Ser Thr Gly
65                  70                  75                  80
Leu Cys Leu Leu Val Met Phe Phe Met Val Leu Val Ala Leu Val Gly
                85                  90                  95
Leu Gly Leu Gly Met Phe Gln Leu Phe His Leu Gln Lys Glu Leu Ala
                100                 105                 110
Glu Leu Arg Glu Ser Thr Ser Gln Met His Thr Ala Ser Ser Leu Glu
                115                 120                 125
Lys Gln Ile Gly His Pro Ser Pro Pro Pro Glu Lys Lys Glu Leu Arg
                130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
                180                 185                 190
Ser Lys Val Tyr Phe Arg Gly Gln Ser Cys Asn Asn Leu Pro Leu Ser
                195                 200                 205
His Lys Val Tyr Met Arg Asn Ser Lys Tyr Pro Gln Asp Leu Val Met
                210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
                245                 250                 255
Leu Tyr Val Asn Val Ser Glu Leu Ser Leu Val Asn Phe Glu Glu Ser
```

```
                    260                 265                 270
Gln Thr Phe Phe Gly Leu Tyr Lys Leu
            275                 280

<210> SEQ ID NO 31
<211> LENGTH: 193
<212> TYPE: PRT
<213> ORGANISM: Homo sapiens
<220> FEATURE:
<221> NAME/KEY: MISC_FEATURE
<222> LOCATION: (51)..(193)
<223> OTHER INFORMATION: Preferred receptor binding domain
<220> FEATURE:
<221> NAME/KEY: MISC_FEATURE
<222> LOCATION: (56)..(193)
<223> OTHER INFORMATION: Preferred receptor binding domain

<400> SEQUENCE: 31

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 32
<211> LENGTH: 234
<212> TYPE: PRT
<213> ORGANISM: Homo sapiens
<220> FEATURE:
<221> NAME/KEY: MISC_FEATURE
<222> LOCATION: (97)..(234)
<223> OTHER INFORMATION: Preferred receptor binding domain
<220> FEATURE:
<221> NAME/KEY: MISC_FEATURE
<222> LOCATION: (98)..(234)
<223> OTHER INFORMATION: Preferred receptor binding domain
<220> FEATURE:
<221> NAME/KEY: MISC_FEATURE
<222> LOCATION: (102)..(234)
<223> OTHER INFORMATION: Preferred receptor binding domain

<400> SEQUENCE: 32

Met Asp Pro Gly Leu Gln Gln Ala Leu Asn Gly Met Ala Pro Pro Gly
```

```
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230
```

<210> SEQ ID NO 33
<211> LENGTH: 254
<212> TYPE: PRT
<213> ORGANISM: Homo sapiens
<220> FEATURE:
<221> NAME/KEY: MISC_FEATURE
<222> LOCATION: (86)..(254)
<223> OTHER INFORMATION: Preferred receptor binding domain

<400> SEQUENCE: 33

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125
```

```
Asp Thr Lys Glu Leu Val Val Ala Lys Ala Gly Val Tyr Tyr Val Phe
            130                 135                 140

Phe Gln Leu Glu Leu Arg Arg Val Val Ala Gly Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 34
<211> LENGTH: 281
<212> TYPE: PRT
<213> ORGANISM: Homo sapiens

<400> SEQUENCE: 34

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
                35                  40                  45

Tyr Ser Lys Ser Gly Ile Ala Cys Phe Leu Lys Glu Asp Asp Ser Tyr
            50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
            210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255
```

-continued

```
Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 35
<211> LENGTH: 317
<212> TYPE: PRT
<213> ORGANISM: Homo sapiens
<220> FEATURE:
<221> NAME/KEY: MISC_FEATURE
<222> LOCATION: (161)..(317)
<223> OTHER INFORMATION: Preferred receptor binding domain

<400> SEQUENCE: 35

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 36
```

```
<211> LENGTH: 249
<212> TYPE: PRT
<213> ORGANISM: Homo sapiens
<220> FEATURE:
<221> NAME/KEY: MISC_FEATURE
<222> LOCATION: (103)..(249)
<223> OTHER INFORMATION: Preferred receptor binding domain
<220> FEATURE:
<221> NAME/KEY: MISC_FEATURE
<222> LOCATION: (104)..(249)
<223> OTHER INFORMATION: Preferred receptor binding domain
<220> FEATURE:
<221> NAME/KEY: MISC_FEATURE
<222> LOCATION: (105)..(249)
<223> OTHER INFORMATION: Preferred receptor binding domain

<400> SEQUENCE: 36

Met Ala Ala Arg Arg Ser Gln Arg Arg Arg Gly Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 37
<211> LENGTH: 247
<212> TYPE: PRT
<213> ORGANISM: Homo sapiens
<220> FEATURE:
<221> NAME/KEY: MISC_FEATURE
<222> LOCATION: (112)..(247)
<223> OTHER INFORMATION: Preferred receptor binding domain

<400> SEQUENCE: 37

Met Pro Ala Ser Ser Pro Phe Leu Leu Ala Pro Lys Gly Pro Pro Gly
1               5                   10                  15
```

```
Asn Met Gly Gly Pro Val Arg Glu Pro Ala Leu Ser Val Ala Leu Trp
             20                  25                  30

Leu Ser Trp Gly Ala Ala Leu Gly Ala Val Ala Cys Ala Met Ala Leu
         35                  40                  45

Leu Thr Gln Gln Thr Glu Leu Gln Ser Leu Arg Arg Glu Val Ser Arg
     50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Leu
                245

<210> SEQ ID NO 38
<211> LENGTH: 250
<212> TYPE: PRT
<213> ORGANISM: Homo sapiens
<220> FEATURE:
<221> NAME/KEY: MISC_FEATURE
<222> LOCATION: (112)..(250)
<223> OTHER INFORMATION: Preferred receptor binding domain

<400> SEQUENCE: 38

Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
             20                  25                  30

Leu Ser Trp Gly Ala Ala Leu Gly Ala Val Ala Cys Ala Met Ala Leu
         35                  40                  45

Leu Thr Gln Gln Thr Glu Leu Gln Ser Leu Arg Arg Glu Val Ser Arg
     50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
```

```
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 39
<211> LENGTH: 285
<212> TYPE: PRT
<213> ORGANISM: Homo sapiens
<220> FEATURE:
<221> NAME/KEY: MISC_FEATURE
<222> LOCATION: (140)..(285)
<223> OTHER INFORMATION: Preferred receptor binding domain

<400> SEQUENCE: 39

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220
```

```
Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
            245                 250                 255

Asp Glu Leu Gln Leu Ala Ile Pro Arg Glu Asn Ala Gln Ile Ser Leu
        260                 265                 270

Asp Gly Asp Val Thr Phe Phe Gly Ala Leu Lys Leu Leu
        275                 280                 285

<210> SEQ ID NO 40
<211> LENGTH: 240
<212> TYPE: PRT
<213> ORGANISM: Homo sapiens
<220> FEATURE:
<221> NAME/KEY: MISC_FEATURE
<222> LOCATION: (91)..(240)

<400> SEQUENCE: 40

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 41
<211> LENGTH: 251
<212> TYPE: PRT
<213> ORGANISM: Homo sapiens
<220> FEATURE:
<221> NAME/KEY: MISC_FEATURE
<222> LOCATION: (91)..(251)
<223> OTHER INFORMATION: Preferred receptor binding domain
<220> FEATURE:
<221> N -continued
<223> OTHER INFORMATION: Preferred receptor binding domain

<400> SEQUENCE: 41

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 42
<211> LENGTH: 177
<212> TYPE: PRT
<213> ORGANISM: Homo sapiens
<220> FEATURE:
<221> NAME/KEY: MISC_FEATURE
<222> LOCATION: (52)..(177)
<223> OTHER INFORMATION: Preferred receptor binding domain

<400> SEQUENCE: 42

```
Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
        35                  40                  45

Leu Gln Leu Glu Thr Ala Lys Glu Pro Cys Met Ala Lys Phe Gly Pro
    50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu
```

```
                        85                  90                  95
Ile Tyr Gly Gln Val Ala Pro Asn Ala Asn Tyr Asn Asp Val Ala Pro
                100                 105                 110

Phe Glu Val Arg Leu Tyr Lys Asn Lys Asp Met Ile Gln Thr Leu Thr
            115                 120                 125

Asn Lys Ser Lys Ile Gln Asn Val Gly Gly Thr Tyr Glu Leu His Val
        130                 135                 140

Gly Asp Thr Ile Asp Leu Ile Phe Asn Ser His Gln Val Leu Lys
145                 150                 155                 160

Asn Asn Thr Tyr Trp Gly Ile Ile Leu Leu Ala Asn Pro Gln Phe Ile
                165                 170                 175

Ser

<210> SEQ ID NO 43
<211> LENGTH: 391
<212> TYPE: PRT
<213> ORGANISM: Homo sapiens
<220> FEATURE:
<221> NAME/KEY: MISC_FEATURE
<222> LOCATION: (245)..(391)
<223> OTHER INFORMATION: Preferred receptor binding domain

<400> SEQUENCE: 43

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Ala Glu Ser Arg Leu Gly

-continued

```
                         260                 265                 270
Asp Trp Ser Arg Ile Thr Met Asn Pro Lys Val Phe Lys Leu His Pro
                275                 280                 285

Arg Ser Gly Glu Leu Glu Val Leu Val Asp Gly Thr Tyr Phe Ile Tyr
        290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
        340                 345                 350

Leu Leu Lys Ala Arg Gln Lys Ile Ala Val Lys Met Val His Ala Asp
                355                 360                 365

Ile Ser Ile Asn Met Ser Lys His Thr Thr Phe Phe Gly Ala Ile Arg
        370                 375                 380

Leu Gly Glu Ala Pro Ala Ser
385                 390

<210> SEQ ID NO 44
<211> LENGTH: 389
<212> TYPE: PRT
<213> ORGANISM: Homo sapiens
<220> FEATURE:
<221> NAME/KEY: MISC_FEATURE
<222> LOCATION: (245)..(389)
<223> OTHER INFORMATION: Preferred receptor binding domain

<400> SEQUENCE: 44

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
                20                  25                  30

Arg Ala Gly Glu Gly Asn Ser Cys Leu Leu Phe Leu Gly Phe Phe Gly
            35                  40                  45

Leu Ser Leu Ala Leu His Leu Leu Thr Leu Cys Cys Tyr Leu Glu Leu
50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
                100                 105                 110

Gln Gln Pro Leu Glu Pro Gly Glu Ala Ala Leu His Ser Asp Ser Gln
            115                 120                 125

Asp Gly His Gln Met Ala Leu Leu Asn Phe Phe Phe Pro Asp Glu Lys
130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
            195                 200                 205

Pro Gly Thr Thr Val Met Gly Pro Pro Gly Pro Pro Gly Pro Pro Gly
        210                 215                 220
```

```
Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
            245                 250                 255

Gly Ser Ala Ile Gln Val Lys Asn Asp Leu Ser Gly Val Leu Asn
        260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
        290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
            340                 345                 350

Lys Ala Arg Gln Lys Ile Ala Val Lys Met Val His Ala Asp Ile Ser
        355                 360                 365

Ile Asn Met Ser Lys His Thr Thr Phe Phe Gly Ala Ile Arg Leu Gly
        370                 375                 380

Glu Ala Pro Ala Ser
385

<210> SEQ ID NO 45
<211> LENGTH: 45
<212> TYPE: PRT
<213> ORGANISM: Artificial Sequence
<220> FEATURE:
<223> OTHER INFORMATION: Exemplary glycine/serine linker
<220> FEATURE:
<221> NAME/KEY: MISC_FEATURE
<222> LOCATION: (1)..(1)
<223> OTHER INFORMATION: Gly (when a=1, 2, 3, 4, or 5) or absent (when
      a=0)
<220> FEATURE:
<221> NAME/KEY: MISC_FEATURE
<222> LOCATION: (2)..(2)
<223> OTHER INFORMATION: Ser (when a=1, 2, 3, 4, or 5) or absent (when
      a=0)
<220> FEATURE:
<221> NAME/KEY: MISC_FEATURE
<222> LOCATION: (3)..(3)
<223> OTHER INFORMATION: Ser (when a=1, 2, 3, 4, or 5) or absent (when
      a=0)
<220> FEATURE:
<221> NAME/KEY: MISC_FEATURE
<222> LOCATION: (4)..(4)
<223> OTHER INFORMATION: Gly (when a=2, 3, 4, or 5) or absent (when a=0
      or 1)
<220> FEATURE:
<221> NAME/KEY: MISC_FEATURE
<222> LOCATION: (5)..(5)
<223> OTHER INFORMATION: Ser (when a=2, 3, 4, or 5) or absent (when a=0
      or 1)
<220> FEATURE:
<221> NAME/KEY: MISC_FEATURE
<222> LOCATION: (6)..(6)
<223> OTHER INFORMATION: Ser (when a=2, 3, 4, or 5) or absent (when a=0
      or 1)
<220> FEATURE:
<221> NAME/KEY: MISC_FEATURE
<222> LOCATION: (7)..(7)
<223> OTHER INFORMATION: Gly (when a=3, 4, or 5) or absent (when a=0, 1,
      or 2)
<220> FEATURE:
<221> NAME/KEY: MISC_FEATURE
<222> LOCATION: (8)..(8)
<223> OTHER INFORMATION: Ser (when a=3, 4, or 5) or absent (when a=0, 1,
      or 2)
```

```
<220> FEATURE:
<221> NAME/KEY: MISC_FEATURE
<222> LOCATION: (9)..(9)
<223> OTHER INFORMATION: Ser (when a=3, 4, or 5) or absent (when a=0, 1,
      or 2)
<220> FEATURE:
<221> NAME/KEY: MISC_FEATURE
<222> LOCATION: (10)..(10)
<223> OTHER INFORMATION: Gly (when a=4 or 5) or absent (when a=0, 1, 2,
      or 3)
<220> FEATURE:
<221> NAME/KEY: MISC_FEATURE
<222> LOCATION: (11)..(11)
<223> OTHER INFORMATION: Ser (when a=4 or 5) or absent (when a=0, 1, 2,
      or 3)
<220> FEATURE:
<221> NAME/KEY: MISC_FEATURE
<222> LOCATION: (12)..(12)
<223> OTHER INFORMATION: Ser (when a=4 or 5) or absent (when a=0, 1, 2,
      or 3)
<220> FEATURE:
<221> NAME/KEY: MISC_FEATURE
<222> LOCATION: (13)..(13)
<223> OTHER INFORMATION: Gly (when a=5) or absent (when a=0, 1, 2, 3, or
      4)
<220> FEATURE:
<221> NAME/KEY: MISC_FEATURE
<222> LOCATION: (14)..(14)
<223> OTHER INFORMATION: Ser (when a=5) or absent (when a=0, 1, 2, 3, or
      4)
<220> FEATURE:
<221> NAME/KEY: MISC_FEATURE
<222> LOCATION: (15)..(15)
<223> OTHER INFORMATION: Ser (when a=5) or absent (when a=0, 1, 2, 3, or
      4)
<220> FEATURE:
<221> NAME/KEY: MISC_FEATURE
<222> LOCATION: (16)..(16)
<223> OTHER INFORMATION: Ser (when b=1, 2, 3, 4, or 5) or absent (when
      b=0)
<220> FEATURE:
<221> NAME/KEY: MISC_FEATURE
<222> LOCATION: (17)..(17)
<223> OTHER INFORMATION: Ser (when b=1, 2, 3, 4, or 5) or absent (when
      b=0)
<220> FEATURE:
<221> NAME/KEY: MISC_FEATURE
<222> LOCATION: (18)..(18)
<223> OTHER INFORMATION: Gly (when b=1, 2, 3, 4, or 5) or absent (when
      b=0)
<220> FEATURE:
<221> NAME/KEY: MISC_FEATURE
<222> LOCATION: (19)..(19)
<223> OTHER INFORMATION: Ser (when b=2, 3, 4, or 5) or absent (when b=0
      or 1)
<220> FEATURE:
<221> NAME/KEY: MISC_FEATURE
<222> LOCATION: (20)..(20)
<223> OTHER INFORMATION: Ser (when b=2, 3, 4, or 5) or absent (when b=0
      or 1)
<220> FEATURE:
<221> NAME/KEY: MISC_FEATURE
<222> LOCATION: (21)..(21)
<223> OTHER INFORMATION: Gly (when b=2, 3, 4, or 5) or absent (when b=0
      or 1)
<220> FEATURE:
<221> NAME/KEY: MISC_FEATURE
<222> LOCATION: (22)..(22)
<223> OTHER INFORMATION: Ser (when b=3, 4, or 5) or absent (when b=0, 1,
      or 2)
<220> FEATURE:
<221> NAME/KEY: MISC_FEATURE
<222> LOCATION: (23)..(23)
<223> OTHER INFORMATION: Ser (when b=3, 4, or 5) or absent (when b=0, 1,
      or 2)
<220> FEATURE:
<221> NAME/KEY: MISC_FEATURE
```

-continued

```
<222> LOCATION: (24)..(24)
<223> OTHER INFORMATION: Gly (when b=3, 4, or 5) or absent (when b=0, 1,
      or 2)
<220> FEATURE:
<221> NAME/KEY: MISC_FEATURE
<222> LOCATION: (25)..(25)
<223> OTHER INFORMATION: Ser (when b=4 or 5) or absent (when b=0, 1, 2,
      or 3)
<220> FEATURE:
<221> NAME/KEY: MISC_FEATURE
<222> LOCATION: (26)..(26)
<223> OTHER INFORMATION: Ser (when b=4 or 5) or absent (when b=0, 1, 2,
      or 3)
<220> FEATURE:
<221> NAME/KEY: MISC_FEATURE
<222> LOCATION: (27)..(27)
<223> OTHER INFORMATION: Gly (when b=4 or 5) or absent (when b=0, 1, 2,
      or 3)
<220> FEATURE:
<221> NAME/KEY: MISC_FEATURE
<222> LOCATION: (28)..(28)
<223> OTHER INFORMATION: Ser (when b=5) or absent (when b=0, 1, 2, 3, or
      4)
<220> FEATURE:
<221> NAME/KEY: MISC_FEATURE
<222> LOCATION: (29)..(29)
<223> OTHER INFORMATION: Ser (when b=5) or absent (when b=0, 1, 2, 3, or
      4)
<220> FEATURE:
<221> NAME/KEY: MISC_FEATURE
<222> LOCATION: (30)..(30)
<223> OTHER INFORMATION: Gly (when b=5) or absent (when b=0, 1, 2, 3, or
      4)
<220> FEATURE:
<221> NAME/KEY: MISC_FEATURE
<222> LOCATION: (31)..(31)
<223> OTHER INFORMATION: Gly (when c=1, 2, 3, 4, or 5) or absent (when
      c=0)
<220> FEATURE:
<221> NAME/KEY: MISC_FEATURE
<222> LOCATION: (32)..(32)
<223> OTHER INFORMATION: Ser (when c=1, 2, 3, 4, or 5) or absent (when
      c=0)
<220> FEATURE:
<221> NAME/KEY: MISC_FEATURE
<222> LOCATION: (33)..(33)
<223> OTHER INFORMATION: Gly (when c=2, 3, 4, or 5) or absent (when c=0
      or 1)
<220> FEATURE:
<221> NAME/KEY: MISC_FEATURE
<222> LOCATION: (34)..(34)
<223> OTHER INFORMATION: Ser (when c=2, 3, 4, or 5) or absent (when c=0
      or 1)
<220> FEATURE:
<221> NAME/KEY: MISC_FEATURE
<222> LOCATION: (35)..(35)
<223> OTHER INFORMATION: Gly (when c=3, 4, or 5) or absent (when c=0, 1,
      or 2)
<220> FEATURE:
<221> NAME/KEY: MISC_FEATURE
<222> LOCATION: (36)..(36)
<223> OTHER INFORMATION: Ser (when c=3, 4, or 5) or absent (when c=0, 1,
      or 2)
<220> FEATURE:
<221> NAME/KEY: MISC_FEATURE
<222> LOCATION: (37)..(37)
<223> OTHER INFORMATION: Gly (when c=4 or 5) or absent (when c=0, 1, 2,
      or 3)
<220> FEATURE:
<221> NAME/KEY: MISC_FEATURE
<222> LOCATION: (38)..(38)
<223> OTHER INFORMATION: Ser (when c=4 or 5) or absent (when c=0, 1, 2,
      or 3)
<220> FEATURE:
<221> NAME/KEY: MISC_FEATURE
<222> LOCATION: (39)..(39)
<223> OTHER INFORMATION: Gly (when c=5) or absent (when c=0, 1, 2, 3, or
      4)
<220> FEATURE:
<221> NAME/KEY: MISC_FEATURE
```

```
<222> LOCATION: (40)..(40)
<223> OTHER INFORMATION: Ser (when c=5) or absent (when c=0, 1, 2, or
      4)
<220> FEATURE:
<221> NAME/KEY: MISC_FEATURE
<222> LOCATION: (41)..(41)
<223> OTHER INFORMATION: Ser (when d=1, 2, 3, 4, or 5) or absent (when
      d=0)
<220> FEATURE:
<221> NAME/KEY: MISC_FEATURE
<222> LOCATION: (42)..(42)
<223> OTHER INFORMATION: Ser (when d=2, 3, 4, or 5) or absent (when d=0
      or 1)
<220> FEATURE:
<221> NAME/KEY: MISC_FEATURE
<222> LOCATION: (43)..(43)
<223> OTHER INFORMATION: Ser (when d=3, 4, or 5) or absent (when d=0, 1,
      or 2)
<220> FEATURE:
<221> NAME/KEY: MISC_FEATURE
<222> LOCATION: (44)..(44)
<223> OTHER INFORMATION: Ser (when d=4 or 5) or absent (when d=0, 1, 2,
      or 3)
<220> FEATURE:
<221> NAME/KEY: MISC_FEATURE
<222> LOCATION: (45)..(45)
<223> OTHER INFORMATION: Ser (when d=5) or absent (when d=0, 1, 2, 3, or
      4)

<400> SEQUENCE: 45

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

<210> SEQ ID NO 46
<211> LENGTH: 11
<212> TYPE: PRT
<213> ORGANISM: Artificial Sequence
<220> FEATURE:
<223> OTHER INFORMATION: Glycine/serine linker

<400> SEQUENCE: 46

Gly Ser Ser Gly Ser Ser Gly Ser Ser Gly Ser
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Glycine/serine linker

<400> SEQUENCE: 47

Ser Ser Gly Ser Ser Gly Ser Ser Gly Ser
1               5                   10
```